(12) United States Patent
Giannessi et al.

(10) Patent No.: US 7,375,124 B2
(45) Date of Patent: *May 20, 2008

(54) USE OF α-PHENYLTHIOCARBOXYLIC AND α-PHENYLOXYCARBOXYLIC ACIDS WITH SERUM-GLUCOSE-LOWERING AND SERUM-LIPID-LOWERING ACTIVITY

(75) Inventors: Fabio Giannessi, Pomezia (IT); Emanuela Tassoni, Pomezia (IT); Maria Ornella Tinti, Pomezia (IT); Pompeo Pessotto, Pomezia (IT); Natalina Dell'Uomo, Pomezia (IT); Anna Floriana Sciarroni, Pomezia (IT); Tiziana Brunetti, Pomezia (IT); Ferdinando Maria Milazzo, Pomezia (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 0 days.

This patent is subject to a terminal disclaimer.

(21) Appl. No.: 10/539,833

(22) PCT Filed: Dec. 16, 2003

(86) PCT No.: PCT/IT03/00820

§ 371 (c)(1),
(2), (4) Date: Jul. 19, 2005

(87) PCT Pub. No.: WO2004/056355

PCT Pub. Date: Jul. 8, 2004

(65) Prior Publication Data

US 2006/0154979 A1 Jul. 13, 2006

(30) Foreign Application Priority Data

Dec. 19, 2002 (IT) .......................... RM2002A0629

(51) Int. Cl.
*A61K 31/425* (2006.01)
*A61K 31/42* (2006.01)

(52) U.S. Cl. ..................... 514/369; 514/376; 548/226; 548/183

(58) Field of Classification Search ................. 514/369, 514/376
See application file for complete search history.

(56) References Cited

U.S. PATENT DOCUMENTS 3,262,850 A 7/1966 Jones et al.

FOREIGN PATENT DOCUMENTS

GB 1 422 679 A 1/1976
WO 03 059875 A 7/2003

OTHER PUBLICATIONS

Communication dated Jan. 13, 2006 in EP 03 780 669.2—2123 from the European Patent Office.

D. Winegar et al., "Role of peroxisome proliferators-activated receptors in atherosclerosis", Current Opinion In Cardiovascular, Plumonary and Renal Investigational Drugs, 2000, vol. 2, No. 3, pp. 233-243, XP008029337.

D. Brooks et al., "Design and synthesis of 2-methyl-2-{4-'2-(5-methyl-2-aryloxazol-4-yl)ethoxy!pheonxy }propionic acids: a new class of dual PPARalpha/gamma agonists", Journal of Medicinal Chemistry, American Chemical Society, vol 44, No. 13, Jun. 21, 2001, pp. 2061-2064, XP002184099.

I. Lalezari et al., "LR-16 A compound with potent effects on the oxygen affinity of hemoglobin on blood cholesterol and on low density lipoprotein", Proceedings of the national academy of sciences of the United States, vol. 85, No. 16, 1988, pp. 6117-6121, XP001161155.

S. Gronowitz et al., "Potential Hypolipidemic Agents XIX. Synthesis and lipid-lowering properties of the thiophene derivatives related to clofibrate", ACTA Pharmaceutical Suecica, XX, XX, vol. 15, No. 5, 1978, pp. 361-367, XP01053343.

P. Duriez et al., "Post-Statin Approaches to Hyperlipidaemia", Expert Opinion on Ivenstigationa Drugs, Ashley Publication Ltd., vol. 7, No. 12, Dec. 1998, pp. 1997-2009, XP000892408.

P.J. Brown et al., "U Ureido-Thiobutyric Acid (GW9578) is a subtype-Selective PPARalpha Agonist with Potent lipid-Lowering ASctivity", Journal of Medicinal Chemistry, American Chemical Society, vol. 42, No. 19, Apr. 9, 1999, pp. 3785-3788, XP002128791.

M. Guerre-Millo et al., "Peroxisome proliferators-activated receptor alpha activators improve insulin sensitivity and reduce adiposity", Journal of Biological Chemistry, vol. 275, No. 22, Jun. 2, 2000, pp. 16638-16642, XP002275720.

B. Zhang Bei et al., "New approaches in the treatment of type 2 diabetes", Current Opinion in Chemical Biology, vol. 4, No. 4, Aug. 2000, pp. 461-467, XP002275721.

R. Hawke et al., "Potent hypocholesterolemic activity of novel ureido phenoxyisobutyrates correlates with their intrinsic fibrate potency and not with their ACAT inhibitory activity", Journal of Lipid Research, vol. 38, No. 6, 1997, pp. 1189-1203, XP002275722.

*Primary Examiner*—Ardin H. Marschel
*Assistant Examiner*—Shirley V Gembeh
(74) *Attorney, Agent, or Firm*—Nixon & Vanderhye P.C.

(57) ABSTRACT

The use is described of derivatives of α-phenylthiocarboxylic and α-phenyloxycarboxylic acids with formula (i): in which the substituents have the meanings described in the text, for the preparation of a medicine for the prophylaxis and treatment of diabetes, particularly type 2 diabetes, its complications, the various forms of insulin resistance, and hyperlipidaemias

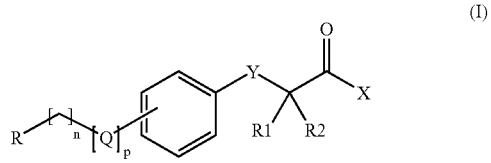

(I)

19 Claims, No Drawings

USE OF α-PHENYLTHIOCARBOXYLIC AND α-PHENYLOXYCARBOXYLIC ACIDS WITH SERUM-GLUCOSE-LOWERING AND SERUM-LIPID-LOWERING ACTIVITY

This application is the U.S. national phase of international application PCT/IT2003/000820 filed 16 Dec. 2003 which designated the U.S. and claims benefit of IT RM2002A000629, dated 19 Dec. 2002, the entire contents of each of which are hereby incorporated by reference.

The invention described herein relates to the use of derivatives of α-phenylthiocarboxylic and α-phenyloxycarboxylic acids for the preparation of a medicine of general formula (I) with serum-glucose-lowering and/or serum-lipid-lowering activity.

BACKGROUND TO THE INVENTION

Diabetes is a widespread disease present throughout the world and is associated with major clinical complications including microvascular complications such as diabetic retinopathy, diabetic neuropathy and diabetic nephropathy, and macrovascular complications such as atherosclerosis, peripheral vasculopathies, myocardial infarction and stroke.

The insulin resistance that characterises diabetes is also involved in syndrome X, in polycystic ovary syndrome, in obesity, in hypertension, in hyperlipidaemia and in hypercholesterolaemia (J. Am Osteopath Assoc 2000 October; 100(10):621-34; JAMA 2002 November 27; 288(20):2579-88).

Hyperlipidaemia, hypercholesterolaemia and hypertension are known to play a decisive role in the onset of coronary heart disease (CHD).

An increase in protein glycosylation is also known to be involved in the above-mentioned complications of diabetes (Diabetologia 2001 February; 44(2):129-46).

Said complications constitute a serious threat to the health and well-being of the individual.

Different clinical forms of diabetic disease are known, the most common being type 2 and type 1 diabetes. Type 2 diabetes is characterised by a reduced sensitivity to the action of insulin (insulin resistance) and gives rise to an increase in insulin levels in the body in an attempt to compensate for this defect and to a consequent increase in glucose levels. There have been numerous reports confirming that insulin resistance is involved in many disease conditions other than type 2 diabetes itself, such as dyslipidaemia, obesity, arterial hypertension, fatty liver and certain macrovascular and microvascular characteristics of diabetic disease itself. The association between insulin resistance and obesity, hypertension and dyslipidaemia is known as syndrome X.

For the treatment of type 2 diabetes, a number of drugs have been on the market for some time now such as the biguanides and sulphonylureas. The best known of the biguanides is metformin but its mechanism of action is not clear and it presents side effects such as gastrointestinal disorders and the danger of acidosis in conditions of renal, cardiac, hepatic, pulmonary insufficiency, etc. The sulphonylureas promote the secretion of insulin by the β-cells and have episodes of hypoglycaemia as a possible side effect. In addition, all the monotherapies with sulphonylureas or with metformin are doomed to failure in the long term (UKPDS Study).

Recently introduced onto the market are the thiazolidinediones, which are insulin-sensitising antidiabetic agents such as troglitazone (J. Med. Chem., 1989, 32, 421-428), pioglitazone (Arzneim. Forsch./Drug Res., 1990, 40 (1), 37-42), and rosiglitazone (Bioorg. Med. Chem. Lett., 1994, 4, 1181-1184) which are capable of reducing diabetic hyperglycaemia and insulin levels. The side effects already established for troglitazone and feared for other compounds belonging to this class are: liver toxicity (which has led to the withdrawal of troglitazone from the market in the USA), increased LDL-cholesterol, weight gain and oedema.

These compounds are synthetic ligands with high affinity for Peroxisome Proliferator Activated Receptor γ (PPARγ) (J. Biol. Chem., 1995, 270, 12953-12956).

Peroxisome Proliferator Activated Receptors (PPARs) are receptors belonging to the superfamily of the nuclear receptors whose function is to control the expression of genes involved in carbohydrate and lipid metabolism (J. Med. Chem., 2000, 43, 527-550). Various subtypes of PPARs have been identified: PPARγ, PPARα and PPARβ (also known as 6). The gamma isoform (PPARγ) is involved in the regulation of the differentiation of adipocytes and in energy homeostasis, while the alpha isoform (PPARα) controls the oxidation of fatty acids resulting in modulation of the lipid levels in plasma. It is important to note that the reduction of lipids, which is obtained in rodents with PPARγ agonists such as rosiglitazone, is hardly to be found in human subjects, whereas the lipid reduction caused in rodents by fibrates is confirmed in humans. A correspondence between activation of the PPARγ receptor and serum-glucose-lowering activity has been confirmed in structure-activity relationship studies aimed at identifying new molecules with potential antidiabetic action (J. Med. Chem., 1996, 39, 665-668; J. Med. Chem., 1998, 41, 5020-5036; 5037-5054; 5055-5069). The insulin-sensitising action would appear to be related to the fatty acid recruitment action regulated by the activated PPARγ receptor, which is thought to lead to an improvement in the insulin resistance of the tissues by improving glycaemia and lowering insulin levels (Diabetes, 1998, 47, 507-514).

Over the past few years mixed-profile molecules have emerged, i.e. ligands of PPARγ and PPARα (KRP 297, Diabetes, 1998, 47, 1841-1847; DRF 2725, Diabetes, 2001, 50, suppl. 2, A108; AZ 242, Diabetes, 2001, 50, suppl. 2, A121-A122; WO 01/16120). It is in this context that we should view the very recent publication of a Smithkline Beecham patent (WO 02/067912 published on 6 September 2002) which refers to a new class of compounds defined as "PPAR pan-agonists", i.e. agonists capable of activating all three PPAR isoforms so as to minimise the unwanted side effects of PPARγ activation. In particular, this new class of antidiabetic agents, though maintaining the characteristics typical of PPARγ activation, are thought to lead to less weight gain and milder oedema. These compounds are potentially capable of exerting good control of diabetic disease by presenting a serum-glucose-lowering and serum-lipid-lowering action with fewer of the side effects typical of the first series of compounds in the thiazolidonedione class, which were exclusively ligands of the PPARγ receptor. The structures claimed in patents WO 01/16120 and WO 02/067912 share the characteristic in common that they present a fibrate-like portion.

Not all the scientific community, however, agrees with what has been outlined here above. In fact, studies regarding new-generation compounds, whether thiazolidinedione derivatives or not, (MC555, J. Biol. Chem., 1998, Vol. 273 (49), 32679-32684; NC2100 Diabetes, 2000, 49, 759-767, YM440, Metabolism, 2000, 49, 411-417), in gene transactivation tests, in-vitro experiments on glucose uptake with muscle tissue, and in-vivo experiments in transgenic animals with deficient expression of the PPARγ receptor, have suggested there may be no direct relationship between activation of the PPARγ receptor and the serum-glucose-lowering and serum-lipid-lowering activity of these compounds (*Toxicology Letters*, 2001, 120, 9-19).

By way of confirmation of this, there are a number of investigators who have chosen to use in-vivo screening of diabetic animals (db/db mice, ob/ob mice) in order to identify possible insulin-sensitising agents which are not necessarily good PPAR ligands. From these experiments a number of compounds with interesting antidiabetic activity have been selected and are still in the course of study in animal models (DRF 2189, *J. Med. Chem.*, 1998, 41, 1619-1630; JTT-501, *J. Med. Chem.*, 1998, 41, 1927-1933).

The scientific community would now seem to be oriented towards a search for new compounds with a different mechanism of action which have a similar or superior effect on insulin sensitivity and glucose homeostasis without toxic effects (*J. Med. Chem.*, 2001, 44, 2601-2611) and which are endowed with serum-lipid-lowering activity superior to that of both the old and new antidiabetic agents currently in use.

Hyperlipidaemia is a severe aspect of diabetic disease, constituting, together with the hypertension that is often present, a risk factor for atherosclerosis and for cardiovascular disease which is the first cause of death in diabetes.

The need to reduce the lipids in the blood is often tackled using fibrates, which, despite the positive results obtained in insulin resistance, have never proved successful as serum-glucose-lowering agents.

SUMMARY OF THE INVENTION

It has now been found that the compounds of formula (I) described here below are agents which are active as serum-glucose-lowering and/or serum-lipid-lowering agents capable, in particular, of increasing HDL-cholesterol levels.

The formula (I) compounds are endowed with low toxicity and are therefore useful for the treatment of hyperglycaemia and/or hyperlipidaemia and for increasing HDL-cholesterol levels.

Preferred applications are the prophylaxis and treatment of diabetes, particularly type 2 diabetes, the microvascular complications of diabetes, such as diabetic retinopathy, diabetic neuropathy and diabetic nephropathy, the macrovascular complications of diabetes such as atherosclerosis, peripheral vasculopathy, myocardial infarction, stroke, syndrome X, polycystic ovary syndrome, obesity, hyperlipidaemia, hypercholesterolaemia, hypertension, the various forms of insulin resistance, fatty liver, particularly NAFLD (non-alcoholic fatty liver disease) and NASH (non-alcoholic steatohepatitis) and the primary and secondary prevention of coronary heart disease (CHD).

One object of the present invention is therefore the use of formula (I) compounds:

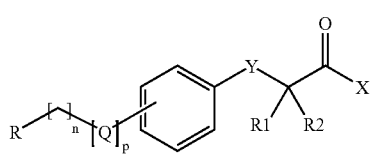

(I)

in which:

R is —H; aryl or heteroaryl, mono, bicyclic or tricyclic, possibly substituted with one or more halogen groups, nitro, hydroxy, alkyl and alkoxy, possibly substituted with one or more halogen groups;

n is 0-3;

p is 0-1;

X is —OH, —O-alkyl $C_1$-$C_4$;

R1 and R2, which may be the same or different, are selected from: —H; alkyl $C_1$-$C_5$, —COX;

Q is selected from: NH, O, S, —NHC(O)O—, NHC(O)NH—, —NHC(O)S—, —OC(O)NH—, —NHC(S)O—, —NHC(S)NH—, —C(O)NH—;

and Y is O, S;

and their pharmaceutically acceptable salts, racemic mixtures, single enantiomers, stereoisomers or geometric isomers, and tautomers, for the preparation of a medicine for the prophylaxis and treatment of diabetes, particularly type 2 diabetes; of the microvascular complications of diabetes, such as diabetic retinopathy, diabetic neuropathy and diabetic nephropathy; of the macrovascular complications of diabetes, such as atherosclerosis peripheral vasculopathy, myocardial infarction and stroke; of syndrome X, polycystic ovary syndrome, obesity, of hyperlipidaemia, hypercholesterolaemia, hypertension, and the various forms of insulin resistance; of fatty liver, particularly NAFLD (non-alcoholic is fatty liver disease) and NASH (non-alcoholic steatohepatitis); for the primary and secondary prevention of coronary heart disease (CHD), and for increasing HDL-cholesterol levels.

Further objects of the present invention are pharmaceutical compositions containing as their active ingredient one or more formula (I) compounds and at least one pharmaceutically acceptable diluent and/or excipient.

DETAILED DESCRIPTION OF THE INVENTION

Among the formula (I) compounds a first group of preferred compounds consists in compounds in which R is an aryl, possibly substituted with one or more halogen atoms, alkyl, alkoxy or haloalkyl, preferably methyl, methoxy or trifluoromethyl, nitro, mono- o di-alkylamine.

Within the context of this first group, preferably p is 1, n is 0, 1 or 2, and Q is oxygen.

A second group of preferred compounds consists of compounds in which R is a heteroaryl, preferably containing nitrogen as heteroatom, e.g. indole and carbazole, bound to the rest of the molecule via all the positions allowed; particularly preferred among these are the 1-indolyl and 1-carbazolyl.

Within the context of this second group. Preferably p is 1, n is 0, 1 or 2, and Q is oxygen.

Particularly preferred are the following compounds prepared according to the general methods and synthesis procedures described here below, which illustrate, but in no way limit the applicability of the invention:

i. methyl 2-[3-[2-(4-chlorophenyl)ethoxy]phenylthio]isobutyrate (ST2195);

ii. 2-[3-[2-(4-chlorophenyl)ethoxy]phenylthio]-2-methylpropanoic acid (ST2518);

iii. methyl 2-[4-[2-(4-chlorophenyl)ethoxy]phenylthio]isobutyrate (ST1929);

iv. methyl 2-[3-(2-(2,4-dichlorophenyl)ethoxy)phenylthio]isobutyrate (ST2534);

v. methyl 2-[4-(2-(2,4-dichlorophenyl)ethoxy)phenylthio] isobutyrate (ST2531);
vi. methyl 2-[3-(2-(carbazol-9-yl)ethoxy)phenylthio] isobutyrate (ST2365);
vii. methyl 2-[4-(2-(carbazol-9-yl)ethoxy)phenylthio] isobutyrate (ST2387);
viii. methyl 2-[4-[2-(1-indolyl)ethoxy]phenylthio]isobutyrate (ST1983);
ix. methyl 2-[3-[2-(1-indolyl)ethoxy]phenylthio]isobutyrate (ST2394);
x. methyl 2-[3-[2-(2-naphthyl)ethoxy]phenylthio]iso-butyrate (ST2167);
xi. methyl 2-[4-[2-(2-naphthyl)ethoxy]phenylthio]isobutyrate (ST2011).
xii. 2-[4-[2-(4-chlorophenyl)ethoxy]phenylthio]-2-methylpropanoic acid (ST2505);
xiii. 2-[3-(2-(2,4-dichlorophenyl)ethoxy)phenylthio]-2-methylpropanoic acid (ST2653);
xiv. 2-[4-(2-(2,4-dichlorophenyl)ethoxy)phenylthio]-2-methylpropanoic acid (ST2652);
xv. 2-[3-(2-(carbazol-9-yl)ethoxy)phenylthio]-2-methyl propanoic acid (ST2618);
xvi. 2-[4-[2-(1-indolyl)ethoxy]phenylthio]-2-methyl propanoic acid (ST2622):
xvii. 2-[3-[2-(1-indolyl)ethoxy]phenyltho]-2-methyl propanoic acid (ST2651);
xviii. 2-[3-[2-(2-naphthyl)ethoxy]phenylthio]-2-methylpropanoic acid (ST2609);
xix. 2-[4-[2-(2-naphthyl)ethoxy]phenylthio]-2-methylpropanoic acid (ST2036);
xx. methyl 2-[4-[2-(1-(5-methoxy)indolil)ethoxy]phenylthio]isobutyrate (ST2577);
xxi. methyl 2-[4-[2-(1-(5-benziloxy)indolil)etoxy]phenylthio]isobutyrate (ST2562);
xxii. methyl 2-[3-[5-(4-nitrophenyl)furfuryloxy]phenylthio]isobutyrate (ST2501);
xxii. 2-[4-[2-(1-(5-methoxy)indolil)ethoxy]phenylthio] isobutiric acid (ST2733);
xxiv. 2-[4-[2-(1-(5-benzyloxy)indolil)ethoxy]phenylthio]-2-methylpropanoic acid (ST2740);
xxv. 2-methyl-2-[3-[5-(4-nitrophenyl)furfuryloxy]phenylthio]proparioic acid (ST2753).

Particularly preferred are compounds ST2518 and ST2195.

The formula (I) compounds are prepared using the reactions described in General Methods A-C.

General Synthesis Methods

The following diagrams illustrate the methods used for the synthesis of the formula (I) compounds.

Unless otherwise specified, the meaning of the various symbols coincides with that given in General Formula (I). The hydrolysis procedure described in Method A can also be applied to the other methods.

Method A

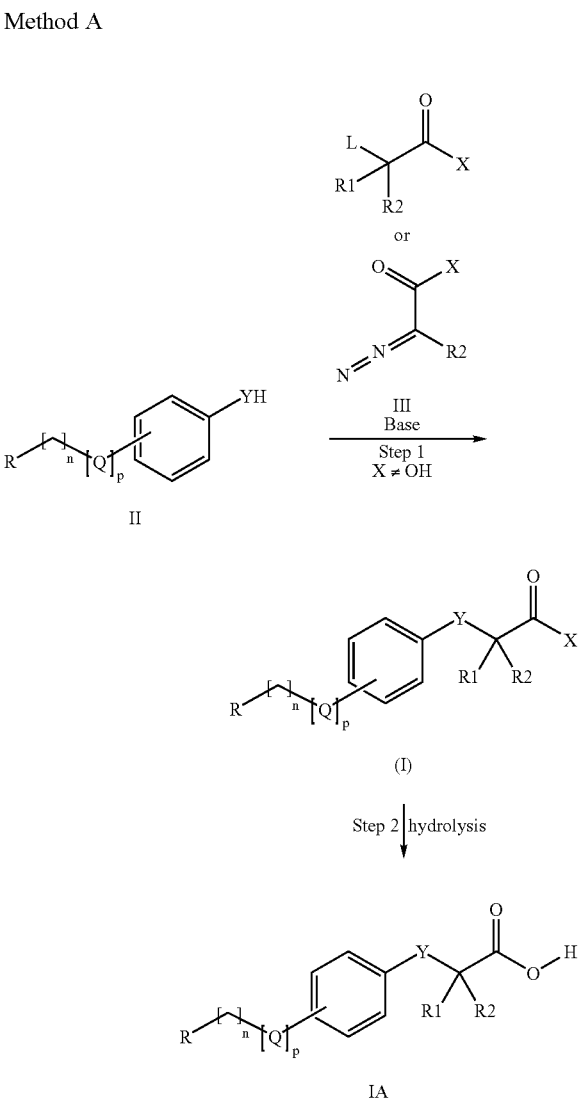

L = leaving group

The preparation of compounds with general formula (I) was done by reacting the general formula II compound with a base, preferably inorganic, and preferably sodium hydride, to form the corresponding anion which was then reacted with a general formula III compound containing an exit group, such as chlorine, bromine, iodine, mesyl, tosyl and diazo (in the case of the diazo group, instead of an inorganic base a bivalent rhodium acetate dimer is used as catalyst), e.g. 2-methyl-alpha-bromoisobutyrate, in a polar solvent such as acetonitrile, toluene, or preferably dimethylformamide, for a time period ranging from 18 to 48 hours at a temperature ranging from 10 to 50° C., preferably 25° C. The product thus obtained was subjected to basic or acid hydrolysis, using, for example, NaOH, or, for example, a mixture of HCl/acetic acid, at a temperature ranging from 10 to 100° C., preferably 25° C., for a time period ranging from 1 to 72 hours, preferably 3 hours, to give the corresponding acid I A.

Method B

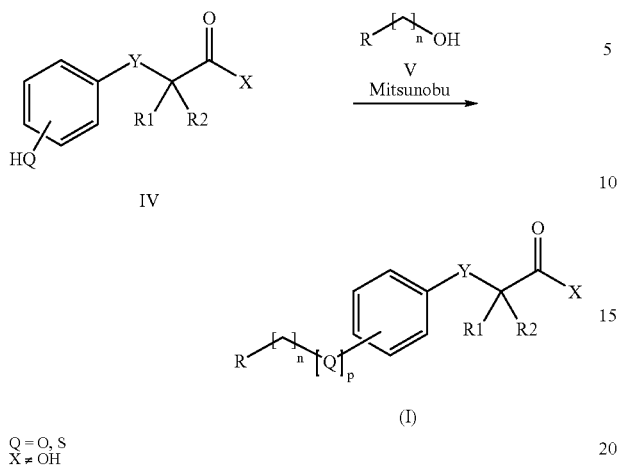

$Q = O, S$
$X \neq OH$

The preparation of general formula (I) compounds was done starting from compounds of general structure IV, which were reacted with an alcohol of general structure V in the classic Mitsunobu reaction conditions, as described in Synthesis 1981, 1-28, using anhydrous and aprotic solvents such as benzene, toluene, ether or preferably tetrahydrofuran, for a time period ranging from 30 minutes to 72 hours, preferably 48 hours, at a temperature ranging from 10 to 40° C., preferable 25° C.

Method C

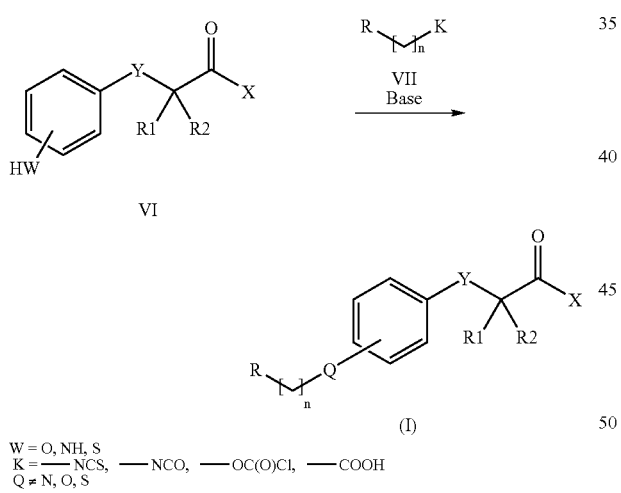

$W = O, NH, S$
$K = $ —NCS, —NCO, —OC(O)Cl, —COOH
$Q \neq N, O, S$

The compounds prepared with this method were obtained starting from VI dissolved in aprotic solvents, for example toluene, ether, benzene, preferably tetrahydrofuran, then added with the related isocyanate, thioisocyanate or chloroformiate VII, possibly in the presence of an inorganic or organic base, preferably triethylamine in a catalytic or stoichiometric amount and leaving it to react for a time period ranging from 6 to 72 hours, preferably 48 hours at temperatures ranging from 10 to 40° C., preferably 25° C. In the case in which K is equal to COOH condensing agents such as diethylphosphorocyanidate, EEDQ, DCC or CDI and the like were used in a ratio of 1:3 equivalents to the substrates, preferably 1:1.5 equivalents, or the process passed through the formation of the acid chloride, conducting the condensation reaction in organic solvents such as DMF, $CH_3CN$, $CHCl_3$, THF and the like, at a temperature ranging from 20 to 80° C., preferably 25° C., with a reaction time ranging from 18 hours to 3 days, preferably 24 hours.

The following examples further illustrate the invention, though by no means exclusively:

EXAMPLE 1

Preparation of methyl 2-[3-[2 (4-chlorophenyl)ethoxy]phenylthio]isobutyrate (ST2195)

Preparation of the intermediate product methyl 2-(3-hydroxyphenylthio)isobutyrate Method A (step 1)

The product was prepared starting from 3-mercaptophenol (2.00 g, 15.9 mmol) in 40 mL of anyhdrous $CH_3CN$, NaH 80% (0.572 g 19.1 mmol) at 0° C. After 5 minutes, methyl-2-bromoisobutyrate (2.88 g, 15.9 mmol) was added to the suspension. The reaction mixture thus obtained was left overnight under magnetic stirring at room temperature. After this period the mixture was poured into $H_2O$ and extracted with ethyl acetate. The organic phase was dried on anhydrous sodium sulphate and evaporated to dryness. The residue obtained was purified by silica gel chromatography using $CHCl_3/CH_3OH$ 98/2 as eluent. 2.900 g of product were obtained (yield: 81%); Mp (melting point): 41.5-42.5° C.; TLC: silica gel, eluent $CHCl_3/CH_3OH$ 98/2, Fr (frontal ratio): 0.23; $^1H$ NMR ($CDCl_3$, 300 MHz) δ: 7.19 (t, 1H), 7.00 (d, 1H), 6.95 (brt, 1H), 6.81 (dd, 1H), 3.69 (s, 3H), 1.50 (s, 6H); HPLC: Column: Inertisil ODS—3 (5 μm) 4.6×250 mm, T: room temperature, mobile phase $CH_3CN/H_2O$ 50/50 (v/v), pH: as is, flow rate: 0.75 mL/min, 205 nm UV detector, retention time 13.82 min; KF: 0.3% $H_2O$; E.A. conforming for $C_{11}H_{14}O_3S$.

Preparation of methyl 2-[3-[2-(4-chlorophenyl) ethoxy]phenylthio]isobutyrate (ST2195)

Method B

The product was prepared starting from methyl 2-(3-hydroxyphenylthio)isobutyrate (prepared as described above) (1.00 g, 4.42 mmol), and 4-chlorophenetyl alcohol (0.692 g, 4.42 mmol) in 15 mL of anhydrous THF, to which were added DIAD (1.16 g, 5.75 mmol) and triphenylphosphine (1.500 g, 5.75 mmol) piecemeal in small portions, keeping the temperature below 30° C. The reaction was left overnight under magnetic stirring at room temperature. After this time period, the solvent was evaporated and the residue purified by silica gel chromatography using hexane/AcOEt 9/1 as eluent. 1.146 g of oily product were obtained (yield: 71%); TLC: silica gel, eluent hexane/AcOEt 9/1, Fr=0.28; $^1H$ NMR ($CDCl_3$, 300 MHz) δ: 7.25 (m, 6H), 7.00 (m, 1H), 6.90 (d, 1H), 4.15 (t, 2H), 3.65 (s, 3H), 3.08 (t, 2H), 1.55 (s, 6H); HPLC: Column: Inertisil ODS 3 (5 μm) 4.6×250 mm, T: 30° C., mobile phase $CH_3CN/H_2O$ 80/20 (v/v), pH: as is, flow rate: 0.75 mL/min, 205 nm UV detector, retention time 19.34 min; KF: 1.7% $H_2O$; E.A. conforming for $C_{19}H_{21}ClO_3S$.

EXAMPLE 2

Preparation of 2-[3-[2-(4-chlorophenyl)ethoxy]phenylthio]-2-methylpropanoic acid (ST2518)

Method A (Step 2)

The product was prepared starting from a solution of ST2195 (prepared as described in example 1) (0.150 g, 0.41 mmol) in 9 mL of methanol to which were added 4 mL of NaOH 1N. The solution thus obtained was left for 48 hours at room temperature under magnetic stirring. After this time period, the solution was diluted with water, acidified with HCl 1N and the aqueous phase extracted with AcOEt. The organic phase was dried on anhydrous $Na_2SO_4$ and filtered and the solvent was evaporated in vacuo. 0.128 g of product were obtained (yield: 88%); Mp: 105-106° C.; TLC: silica gel, eluent $CHCl_3/CH_3OH$ 9.4/0.6, Fr: 0.42; $^1H$ NMR ($CDCl_3$, 300 MHz) δ: 7.45 (m, 5H), 7.10 (m, 2H), 6.80 (dd, 1H), 4.15 (t, 2H), 3.05 (t, 2H), 1.50 (s, 6H); HPLC: Column: Symmetry—$C_{18}$ (5 μm) 4.6×250 mm, T: 30° C., mobile phase $CH_3CN$/ammonium acetate 10 mM 35/65 (v/v), pH: as is, flow rate: 0.80 mL/min, 205 nm UV detector, retention time 4.66 min; E.A. conforming for $C_{18}H_{19}ClO_3S$.

EXAMPLE 3

Preparation of methyl 2-[4-[2-(4-chlorophenyl) ethoxy]phenylthio]isobutyrate (ST1929)

Preparation of the intermediate product methyl 2-(4-hydroxyphenyl-thio)isobutyrate (ST1923)

The title product was prepared according to the procedure described in Method A (step 1) starting from 4-mercaptophenol (0.500 g, 4.0 mmol) in 10 mL of anhydrous $CH_3CN$, to which was added NaH 80% (0.144 g, 4.8 mmol). The mixture was cooled to 0° C. and after 5 minutes methyl-α-bromoisobutyrate (0.724 g, 4.0 mmol) was added. The reaction was left for two days at room temperature under magnetic stirring. After this period, the mixture was poured into $H_2O$ and extracted with ethyl acetate; the aqueous phase was then acidified with HCl 1N and extracted again with ethyl acetate. The pooled organic phases were dried on $Na_2SO_4$, filtered and evaporated. The residue obtained was purified by silica gel chromatography using $CHCl_3$ as eluent. 0.760 g of product were obtained (yield: 84%); Mp: 110-112° C.; TLC: silica gel, eluent $CHCl_3$, Fr: 0.11; $^1H$ NMR ($CDCl_3$, 300 MHz) δ: 7.30 (d, 2H), 6.73 (d, 2H), 5.57 (brm, 1H), 3.70 (s, 3H), 1.45 (s, 6H); HPLC: Column: Symmetry—$C_{18}$, (5 μm) 4.6×250 mm, T: 30° C., mobile phase $CH_3CN/H_2O$ 50/50 (v/v), pH: as is, flow rate: 0.75 mL/min, 205 nm UV detector, retention time 10.14 min; E.A. (elemental analysis) conforming for $C_{11}H_{14}O_3S$.

Preparation of methyl 2-[4-[2-(4-chloro-phenyl) ethoxy]phenylthio]isobutyrate (ST1929)

The title product was prepared according to the procedure described in Method B starting from methyl 2-(4-hydroxyphenylthio)isobutyrate (prepared as described above) (0.800 g, 3.54 mmol) and 4-chlorophenetyl alcohol (0.554 g, 3.54 mmol) in 20 mL of anhydrous THF. DEAD (0.801 g, 4.6 mmol) and triphenylphosphine (1.205 g, 4.6 mmol) were added piecemeal in small portions, maintaining the temperature below 30° C. The reaction was left overnight under magnetic stirring at room temperature. After this period, the solvent was evaporated and the residue purified by silica gel chromatography using hexane/ethyl acetate 9/1 as eluent. 0.416 g of oily product were obtained (yield: 32%); TLC: silica gel, eluent hexane/ethyl acetate 9/1, Fr: 0.32; $^1H$ NMR ($CDCl_3$, 300 MHz) δ: 7.40-7.19 (m, 6H), 6.80 (d, 2H), 4.15 (t, 2H), 3.65 (s, 3H), 3.08 (t, 2H) 1.45 (s, 6H); HPLC: Column: Symmetry—$C_{18}$, (5 μm) 4.6×250 mm, T: 30° C., mobile phase $CH_3CN/H_2O$ 70/30 (v/v), pH: as is, flow rate: 0.75 mL/min, 205 nm UV detector, retention time 31.40 min; KF: 0.4% $H_2O$; E.A. conforming for $C_{19}H_{21}ClO_3S$.

EXAMPLE 4

Preparation of methyl 2-[3-(2-(2,4-dichlorophenyl) ethoxy)phenylthio]isobutyrate (ST2534)

The title product was prepared according to the procedure described in Method B starting from methyl 2-(3-hydroxyphenylthio)iso-butyrate (prepared as described in example 1) (0.280 g, 1.24 mmol) and DIAD (0.325 g, 1.61 mmol) dissolved in 3 mL of anhydrous THF and added dropwise to a solution of 2,4-dichlorophenetylalcohol (0.260 g, 1.36 mmol), and triphenylphosphine (0.422 g, 1.61 mmol) in 4 mL of anhydrous THF at 0° C. The reaction was left overnight under magnetic stirring at room temperature. After this period, the solvent was evaporated and the residue purified by silica gel chromatography using hexane/AcOEt 9.6/0.4 as eluent. 0.327 g of oily product were obtained (yield: 66%); TLC: silica gel, eluent hexane/AcOEt 9/1, Fr: 0.34; $^1H$ NMR ($CDCl_3$, 300 MHz) δ: 7.40 (d, 1H), 7.20 (m, 3H), 7.00 (m, 2H), 6.90 (dd, 1H), 4.15 (t, 2H), 3.65 (s, 3H), 3.20 (t, 2H), 1.45 (s, 6H); HPLC: Column: Inertisil ODS—3 (5 μm) 4.6×250 mm, T: room temperature, mobile phase $CH_3CN/H_2O$ 90/10 (v/v), pH: as is, flow rate: 0.8 mL/min, 205 nm UV detector, retention time 12.40 min; KF: 0.2% $H_2O$; E.A. conforming for $C_{19}H_{20}Cl_2O_3S$.

EXAMPLE 5

Preparation of methyl 2-[4-(2-(2,4-dichlorophenyl) ethoxy)phenylthio]isobutyrate (ST2531)

The title product was prepared according to the procedure described in Method B starting from methyl 2-(4-hydroxyphenylthio)iso-butyrate (prepared as described in example 3) (0.280 g, 1.24 mmol) and DIAD (0.325 g, 1.61 mmol) dissolved in 3 mL of anhydrous THF and added dropwise to a solution of 2,4-dichlorophenetylalcohol (0.260 g, 1.36 mmol) and triphenylphosphine (0.422 g, 1.61 mmol) in 4 mL of anhydrous THF at 0° C. The reaction was left overnight under magnetic stirring at room temperature After this period, the solvent was evaporated and the residue purified by silica gel chromatography using hexane/AcOEt 9.6/0.4 as eluent. 0.346 g of product were obtained (yield: 70%); Mp: 73-74° C.; TLC: silica gel, eluent hexane/AcOEt 9/1, Fr: 0.26; $^1H$ NMR ($CDCl_3$, 300 MHz) δ: 7.35 (m, 3H), 7.22 (m, 2H), 6.83 (d, 2H), 4.18 (t, 2H), 3.65 (s, 3H), 3.20 (t, 2H), 1.45 (s, 6H); HPLC: Column: Inertisil ODS—3 (5 μm) 4.6×250 mm, T: room temperature, mobile phase $CH_3CN/H_2O$. 85/15 (v/v), pH: as is, flow rate: 1 mL/min, 205 nm UV detector, retention time 12.58 min; KF: 0.4% $H_2O$; E.A. conforming for $C_{19}H_{20}Cl_2O_3S$.

EXAMPLE 6

Preparation of methyl 2-[3-(2-(carbazol-9-yl)ethoxy)phenylthio]isobutyrate (ST2365)

The title product was prepared according to the procedure described in Method B starting from methyl 2-(3-hydroxyphenylthio)iso-butyrate (prepared as described in example 1) (0.609 g, 2.7 mmol), 9H-carbazol-9-ethanol (0.570 g, 2.7 mmol), DIAD (0.708 g, 3.5 mmol), and triphenylphosphine (0.917 g, 3.5 mmol) added piecemeal in small portions, keeping the temperature below 30° C., in 14 mL of anhydrous THF. The reaction was left under magnetic stirring for 18 hours at room temperature. After this period, the solvent was evaporated and the residue purified by silica gel chromatography using hexane/AcOEt 9/1 as eluent. 0.510 g of product were obtained (yield: 45%); Mp: 101-103° C.; TLC: silica gel, eluent hexane/AcOEt 8/2, Fr: 0.38; $^1$H NMR (CDCl$_3$, 300 MHz) δ: 8.05 (d, 2H), 7.50 (m, 4H), 7.15 (m, 2H), 7.08 (t, 1H), 7.00 (d, 1H), 6.90 (s, 1H), 6.80 (m, 1H), 4.75 (t, 2H), 4.35 (t, 2H), 3.60 (s, 3H), 1.40 (s, 6H); HPLC: Column: Symmetry—C$_{18}$, (5 μm) 4.6×150 mm, T: room temperature, mobile phase CH$_3$CN/H$_2$O 65/35 (v/v), pH: as is, flow rate: 0.80 mL/min, 205 nm UV detector, retention time 11.45 min; E.A. conforming for C$_{25}$H$_{25}$NO$_3$S.

EXAMPLE 7

Preparation of methyl 2-[4-(2-(carbazol-9-yl)ethoxy)phenylthio]isobutyrate (ST2387)

The product was prepared according to the procedure described in Method B starting from methyl 2-(4-hydroxyphenylthio) isobutyrate (prepared as described in example 3) (0.609 g, 2.7 mmol), 9H-carbazol-9-ethanol (0.570 g, 2.7 mmol), DIAD (0.708 g, 3.5 mmol), and triphenylphosphine (0.917 g, 3.5 mmol) added piecemeal in small portions, keeping the temperature below 30° C., in 14 mL of anhydrous THF. The reaction was left under magnetic stirring for 18 hours at room temperature. After this period, the solvent was evaporated and the residue purified by silica gel chromatography using hexane/AcOEt 9/1 as eluent. 0.702 g of product were obtained (yield: 62%); Mp: 72-74° C.; TLC: silica gel, eluent hexane/AcOEt 8/2, Fr: 0.30; $^1$H NMR (CDCl$_3$, 300 MHz) δ: 8.05 (d, 2H), 7.50 (m, 4H), 7.15 (m, 4H), 6.75 (d, 2H), 4.75 (t, 2H), 4.35 (t, 2H), 3.60 (s, 3H), 1.40 (s, 6H); HPLC: Column: Symmetry—C$_{18}$, (5 μm) 4.6×150 mm, T: room temperature, mobile phase CH$_3$CN/H$_2$O 70/30 (v/v), pH: as is, flow rate: 0.80 mL/min, 205 nm UV detector, retention time 11.60 min; E.A. conforming for C$_{25}$H$_{25}$NO$_3$S.

EXAMPLE 8

Preparation of methyl 2-[4-[2-(1-indolyl)ethoxy]phenylthio]isobutyrate (ST1983)

Preparation of the intermediate product 1-(2-hydroxyethyl)indole

The intermediate product, reported in J. Med. Chem., 1998, 41/10, 1619-1639, was prepared according to the procedure described therein, with the exception of the duration of the reaction time (equal to 30 hours instead of 30 minutes), starting from indole (5.0 g, 42.7 mmol), KOH (3.6 g, 64.1 mmol) and bromoethanol (6.4 g, 51.3 mmol) in 50 ml of anhydrous DMSO, at a temperature of 25-30° C., to obtain 5 g of oily product (yield: 73%).

Preparation of methyl 2-[4-[2-(1-indolyl)ethoxy]phenylthio]isobutyrate (ST1983)

The product was prepared according to the procedure described in Method B starting from methyl 2-(4-hydroxyphenylthio) isobutyrate (prepared as described in example 3) (0.671 g, 2.97 mmol), 1-(2-hydroxyethyl)indole (0.478 g, 2.97 mmol), DEAD (0.672 g, 3.86 mmol), and triphenylphosphine (1.011 g, 3.86 mmol) added piecemeal in small portions, keeping the temperature below 30° C., in 15 mL of anhydrous THF. The reaction was left under magnetic stirring for 48 hours at room temperature. After this period, the solvent was evaporated and the residue purified by silica gel chromatography using hexane/ethyl acetate 8/2 as eluent. In all, 0.500 g of still impure product were obtained which was dissolved in ethyl acetate and washed with a solution of NaOH 1N. The organic phase was dried and evaporated to give a residue of 0.230 g which was purified again by silica gel chromatography, eluting with CHCl$_3$. 0.184 g of oily product were obtained (yield: 17%); TLC: silica gel, eluent hexane/ethyl acetate 8/2, Fr: 0.29; $^1$H NMR (CDCl$_3$, 300 MHz) δ: 7.62 (d, 1H), 7.40-7.10 (m, 6H), 6.78 (d, 2H), 6.50 (d, 1H), 4.50 (m, 2H), 4.24 (m, 2H), 3.61 (s, 3H), 1.40 (s, 6H); HPLC: Column: Symmetry—C$_{18}$, (3.5 μm) 4.6×75 mm, T: room temperature, mobile phase CH$_3$CN/H$_2$O 60/40 (v/v), pH: as is, flow rate: 0.90 mL/min, 205 nm UV detector, retention time 10.70 min; KF: 1.7% H$_2$O; E.A. conforming for C$_{21}$H$_{23}$NO$_3$S.

EXAMPLE 9

Preparation of methyl 2-[3-[2-(1-indolyl)ethoxy]phenylthio]isobutyate (ST2394)

The title product was prepared according the procedure described in Method B starting from methyl 2-(3-hydroxyphenylthio) isobutyrate (prepared as described in example 1) (1.00 g, 4.42 mmol), and 1-(2-hydroxyethyl)indole (prepared as described in example 8) (0.71 μg, 4.42 mmol) in 20 mL of anhydrous THF, to which were added DIAD (1.16 g, 5.75 mmol) and triphenylphosphine (1.500 g, 5.75 mmol) piecemeal in small portions, keeping the temperature below 30° C. The reaction was left overnight under magnetic stirring at room temperature. After this period, the solvent was evaporated and the residue purified by silica gel chromatography using hexane/AcOEt 8/2 as eluent. 0.581 g of oily product were obtained (yield: 35%); TLC: silica gel, eluent hexane/AcOEt 9/1, Fr: 0.22; $^1$H NMR (CDCl$_3$, 300 MHz) δ: 7.62 (d, 1H), 7.42 (d, 1H), 7.30-6.80 (in, 7H), 6.52 (d, 1H), 4.55 (m, 2H), 4.30 (m, 2H), 3.61 (s, 3H), 1.50 (s, 6H); HPLC: Column: Supelco—C$_{18}$ (5 μm) 4.6×150 mm, T: 30° C., mobile phase CH$_3$CN/H$_2$O 70/30 (v/v), pH: as is, flow rate: 0.90 mL/min, 205 nm UV detector, retention time 6.36 min; E.A. conforming for C$_{21}$H$_{23}$NO$_3$S.

EXAMPLE 10

Preparation of methyl 2-[3-[2-(2-naphthyl)ethoxy]phenylthio]isobutyrato (ST2167)

The product was prepared according to the procedure described in Method B (with the exception of DEAD which was replaced by DIAD) starting from methyl 2-(3-hydroxyphenylthio)isobutyrate (prepared as described in example 1) (1.110 g, 4.9 mmol), 2-(2-naphthyl)ethanol (0.842 g, 4.9 mmol), DIAD (1.290 g, 6.37 mmol), and triphenylphosphine (1.670 g, 6.37 mmol) in 20 mL of anhydrous THF. The reaction was left overnight under magnetic stirring at room temperature. After this period, the solvent was evaporated and the residue purified by silica gel chromatography using hexane/AcOEt 7/3 as eluent. The product was further purified by dissolving it in ethyl acetate and washing the organic phase with a solution of $Na_2CO_3$. The organic phase was dried on sodium sulphate and the solvent evaporated in vacuo. 1.14 g of product were obtained (yield: 61.2%); TLC: silica gel, eluent hexane/AcOEt 9/1, Fr: 0.20; $^1$H NMR ($CDCl_3$, 300 MHz) δ: 7.80 (m, 3H), 7.75 (s, 1H), 7.45 (m, 3H), 7.25 (t, 1H), 7.05 (m, 2H), 6.90 (d, 1H), 4.25 (t, 2H), 3.65 (s, 3H), 3.30 (t, 2H), 1.50 (s, 6H); HPLC: Column: Inertisil ODS—3 (5 μm) 4.6×250 mm, T: room temperature, mobile phase $CH_3CN/H_2O$ 80/20 (v/v), pH: as is, flow rate: 0.9 mL/min, 205 nm UV detector, retention time 18.91 min; KF 1.0% $H_2O$; E.A. conforming for $C_{23}H_{24}O_3S$.

EXAMPLE 11

Preparation of methyl 2-[4-[2-(2-naphthyl)ethoxy]phenylthio]isobutyrate (ST2011)

The product was prepared according to the procedure described in Method B starting from methyl 2-(4-hydroxyphenylthio) isobutyrate (prepared as described in example 3) (1.000 g, 4.42 mmol), 2-(2-naphthyl)ethanol (0.760 g, 4.42 mmol), DEAD (1.000 g, 5.75 mmol) and triphenylphosphine (1.500 g, 5.75 mmol) added piecemeal in small portions, maintaining the temperature below 30° C., in 30 mL of anhydrous THF. The reaction was left overnight under magnetic stirring at room temperature. After this period, the solvent was evaporated and the residue purified by silica gel chromatography using hexane/AcOEt 9/1 as eluent. 1.262 g of product (yield: 75%); Mp: 56-57° C.; TLC: silica gel, eluent hexane/AcOEt 9/1, Fr: 0.23; $^1$H NMR ($CDCl_3$, 300 MHz) δ 7.85-7.70 (m, 4H), 7.45-7.28 (m, 5H), 6.83 (d, 2H), 4.27 (t, 2H), 3.65 (s, 3H), 3.26 (t, 2H), 1.45 (s, 6H); HPLC: Column: Inertisil ODS—3 (5 μm) 4.6×250 mm, T: room temperature, mobile phase $CH_3CN/H_2O$ 80/20 (v/v), pH: as is, flow rate: 0.75 mL/min, 205 nm UV detector, retention time 23.51 min; KF: 0.16% $H_2O$; E.A. conforming for $C_{23}H_{24}O_3S$.

EXAMPLE 12

Preparation of 2-[4-[2-(4-chlorophenyl)ethoxy]phenylthio]-2-methylpropanoic acid (ST2505)

Method A (Step 2)

The product was prepared starting from a solution of ST1929 (prepared as described in example 3) (0.572 g, 1.57 mmol) in 36 mL of methanol to which were added 15.7 mL of NaOH 1N. The solution obtained was left overnight under magnetic stirring at reflux temperature. After this period, the solution was acidified with HCl 1N and the aqueous phase extracted with AcOEt. The organic phase was dried on anhydrous $Na_2SO_4$ and filtered and the solvent evaporated in vacuo. The product was purified by chromatography on a silica gel column, eluting with hexane/AcOEt 7:3. 0.448 g of product were obtained (yield: 81.5%); Mp: 87-88° C.; TLC: silica gel, eluent hexane/AcOEt 6/4, Fr: 0.3; $^1$H NMR ($CDCl_3$, 300 MHz) δ: 7.40 (d, 2H), 7.25 (d, 2H), 7.20 (d, 2H), 6.80 (d, 2H), 4.15 (t, 2H), 3.05 (t, 2H), 1.50 (s, 6H); HPLC: Column: Symmetry—$C_{18}$ (5 μm) 4.6×250 mm, T: room temperature, mobile phase $CH_3CN$/ammonium acetate 10 mM 45/55 (v/v), pH: as is, flow rate: 0.70 mL/min, 205 nm UV detector, retention time 4.73 min; E.A. conforming for $C_{18}H_{19}ClO_3S$.

EXAMPLE 13

Preparation of 2-[3-(2-(2,4-dichlorophenyl)ethoxy) phenylthio]-2-methylpropanoic acid (ST2653)

Method A (Step 2)

The product was prepared starting from a solution of ST2534 (prepared as described in example 4) (0.700 g, 1.75 mmol) in 11 mL of $CH_3OH$ to which were added 21 mL of NaOH 1N. The solution obtained was left under magnetic stirring for two days at 40° C. After this period, the $CH_3OH$ was evaporated in vacuo and the aqueous phase was acidified with HCl 1N and extracted with AcOEt. The organic phase was dried on anhydrous $Na_2SO_4$ and filtered and the solvent evaporated in vacuo. 0.486 g of product were obtained (yield: 72%); Mp: 86-88° C.; TLC: silica gel, eluent $CHCl_3/CH_3OH$ 9.6/0.4, Fr: 0.18; $^1$H NMR ($CDCl_3$, 300 MHz) δ: 7.40 (s, 1H), 7.20 (m, 3H), 7.05 (m, 2H), 6.90 (d, 1H), 4.15 (t, 2H), 3.05 (t, 2H), 1.45 (s, 6H); HPLC: Column: Inertisil ODS 3 (5 μm) 4.6×250 mm, T: room temperature, mobile phase $CH_3CN/KH_2PO_4$ 50 mM 70/30 (v/v), pH: appr. 3 ($H_3PO_4$), flow rate: 1 mL/min, 205 nm UV detector, retention time 16.78 min; E.A. conforming for $C_{18}H_{18}C_2O_3S$.

EXAMPLE 14

Preparation of 2-[4-(2-(2,4-dichlorophenyl)ethoxy) phenylthio]-2-methylpropanoic acid (ST2652)

Method A (Step 2)

The product was prepared starting from a solution of ST2531 (prepared as described in example 5) (0.130 g, 0.32 mmol) in 3 mL of tetrahydrofuran, to which were added 3 mL of an aqueous solution of LiOH (0.040 g, 1.67 mmol). The suspension obtained was left overnight under magnetic stirring at room temperature. After this period, the tetrahydrofuran was evaporated in vacuo and the aqueous phase acidified with HCl 1N and extracted with AcOEt. The organic phase was dried on anhydrous $Na_2SO_4$ and filtered and the solvent evaporated in vacuo. The residue obtained was purified on a silica gel chromatography column, eluting with $CHCl_3/CH_3OH$ 9.6/0.4. 0.044 g of product were obtained (yield: 36%); TLC: silica gel, eluent $CHCl_3$/$CH_3OH$ 9.6/0.4, Fr: 0.20; $^1$H NMR ($CDCl_3$, 300 MHz) δ: 7.40 (m, 3H), 7.20 (m, 2H), 6.80 (d, 2H), 4.15 (t, 2H), 3.15 (t, 2H), 1.45 (s, 6H); HPLC: Column: Inertisil ODS 3 (5 μm) 4.6×250 mm, T: room temperature, mobile phase $CH_3CN$/ $KH_2PO_4$ 50 mM 65/35 (v/v), pH: appr. 3 ($H_3PO_4$), flow rate: 1 mL/min, 205 nm UV detector, retention time 27.20 min; E.A. conforming for $C_{18}H_{18}Cl_2O_3S$.

EXAMPLE 15

Preparation of 2-[3-(2-(carbazol-9-yl)ethoxy)phenylthio]-2-methylpropanoic acid (ST2618)

Method A (Step 2)

The product was prepared starting from a solution of ST2365 (prepared as described in example 6) (0.120 g, 0.286 mmol) in 3 mL of tetrahydrofuran, to which was added 1 mL of an aqueous solution of LiOH (0.014 g, 0.5 mmol). The suspension thus obtained was left overnight under magnetic stirring at room temperature. After this period, the tetrahydrofuran was evaporated in vacuo and the aqueous phase acidified with HCl 1N and extracted on anhydrous $Na_2SO_4$ and filtered, and the solvent was evaporated in vacuo. 0.042 g of product were obtained (yield: 36%); TLC: silica gel, eluent $CHCl_3/CH_3OH$ 9.6/0.4, Fr: 0.24; $^1$H NMR ($CDCl_3$, 300 MHz) δ: 8.05 (d, 2H), 7.50 (m, 4H), 7.10-7.00 (m, 5H), 6.80 (d, 1H), 4.70 (t, 2H), 4.30 (t, 2H), 1.50 (s, 6H); HPLC: Column: Inertisil ODS 3 (5 µm) 4.6×250 mm, T: room temperature, mobile phase $CH_3CN/KH_2PO_4$ 50 mM 70/30 (v/v), pH: as is, flow rate: 1 mL/min, 205 nm UV detector, retention time 11.92 min; E.A. conforming for $C_{24}H_{23}NO_3S$.

EXAMPLE 16

Preparation of 2-[4-[2-(1-indolyl)ethoxy]phenylthio]-2-methylpropanoic acid (ST2622)

Method A (Step 2)

The product was prepared starting from a solution of ST1983 (prepared as described in example 8) (1 g, 2.71 mmol) in 15 mL of $CH_3OH$ to which were added 30 mL of NaOH 1N. The solution obtained was left under magnetic stirring for 48 hours at 40° C. After this period, the $CH_3OH$ was evaporated in vacuo and the aqueous phase acidified with HCl 1N and extracted with AcOEt. The organic phase was dried on anhydrous $Na_2SO_4$ and filtered and the solvent evaporated in vacuo. The residue obtained was purified on a silica gel chromatography column, eluting with $CHCl_3/CH_3OH$ 9.6/0.4. 0.679 g of product were obtained (yield: 70%); TLC: silica gel, eluent $CHCl_3/CH_3OH$ 9.6/0.4, Fr: 0.27; $^1$H NMR ($CDCl_3$, 300 MHz) δ: 7.60 (d, 1H), 7.40 (d, 3H), 7.20 (m, 3H), 6.80 (d, 2H), 6.50 (d, 1H), 4.50 (t, 2H), 4.25 (t, 2H), 1.50 (s, 6H); HPLC: Column: Inertisili ODS 3 (5 µm) 4.6×250 mm, T: room temperature, mobile phase $CH_3CN/KH_2PO_4$ 50 mM 70/30 (v/v), pH: as is, flow rate: 1 mL/min, 205 nm UV detector, retention time 8.30 min; E.A. conforming for $C_{20}H_{21}NO_3S$.

EXAMPLE 17

Preparation of 2-[3-[2-(1-indolyl)ethoxy]phenylthio]-2-methylpropanoic acid (ST2651)

Method A (Step 2)

The product was prepared starting from a solution of ST2394 (prepared as described in example 9) (0.140 g, 0.38 mmol) in 3 mL of tetrahydrofuran to which were added 2 mL of an aqueous solution of LiOH (0.040 g, 1.67 mmol). The suspension obtained was left overnight under magnetic stirring at room temperature. After this period the tetrahydrofuran was evaporated in vacuo and the aqueous phase acidified with HCl 1N and extracted with AcOEt. The organic phase was dried on anhydrous $Na_2SO_4$ and filtered and the solvent evaporated in vacuo. The residue obtained was purified on a silica gel chromatography column, eluting with $CHCl_3/CH_3OH$ 9.6/0.4 0.086 g of product were obtained (yield: 63%); TLC: silica gel, eluent $CHCl_3/CH_3OH$ 9.6/0.4, Fr: 0.19; $^1$H NMR ($CDCl_3$, 300 MHz) δ: 7.60 (d, 1H), 7.40 (d, 1H), 7.20-7.00 (m, 6H), 6.80 (d, 1H), 6.50 (d, 1H), 4.50 (t, 2H), 4.20 (t, 2H), 1.50 (s, 6H); HPLC: Column: Inertisil ODS 3 (5 µm) 4.6×250 mm, T: room temperature, mobile phase $CH_3CN/KH_2PO_4$ 50 mM 65/35 (v/v), pH: as is, flow rate: 1 mL/min, 205 nm UV detector, retention time 8.77 min; E.A. conforming for $C_{20}H_{21}NO_3S$.

EXAMPLE 18

Preparation of 2-[3-[2-(2-naphthyl)ethoxy]phenylthio]-2-methylpropanoic acid (ST2609)

Method A (Step 2)

The product was prepared starting from a solution of ST2167 (prepared as described in example 10) (0.270 g, 0.71 mmol) in 18 mL of $CH_3OH$ to which were added 15 mL of NaOH 2N. The solution obtained was left for 48 hours under magnetic stirring at reflux temperature. After this period, the reaction mixture was cooled, acidified with HCl 1N and extracted with AcOEt. The organic phase was dried on anhydrous $Na_2SO_4$ and filtered and the solvent evaporated in vacuo. The residue obtained was purified on a silica gel chromatography column, eluting with hexane/AcOEt 7/3. 0.030 g of product were obtained (yield: 14%); TLC: silica gel, eluent hexane/AcOEt 6/4, Fr: 0.24; $^1$H NMR ($CDCl_3$, 300 MHz) δ: 7.80 (m, 3H), 7.70 (s, 1H), 7.40 (m, 3H), 7.20 (m, 1H), 7.10 (s, 2H), 6.90 (d, 1H), 4.20 (t, 2H), 3.20 (t, 2H), 1.50 (s, 6H); HPLC: Column: Inertisil ODS 3 (5 an) 4.6×250 mm, T: room temperature, mobile phase $CH_3CN/KH_2PO_4$ 50 mM 70/30 (v/v), pH: as is, flow rate: 1 mL/min, 205 nm UV detector, retention time 11.77 min; E.A. conforming for $C_{22}H_{22}O_3S$.

EXAMPLE 19

Preparation of 2-[4-[2-(2-naphthyl)ethoxy]phenylthio]-2-methylpropanoic acid (ST2036)

Method A (Step 2)

The product was, prepared starting from a solution of ST2011 (prepared as described in example 11) (0.498 g, 1.29 mmol) in 30 mL of $CH_3OH$ to which were added 12.9 mL di NaOH 1N. The solution obtained was left overnight under magnetic stirring at reflux temperature. After this time, the reaction mixture was cooled, acidified with HCl 1N and extracted with AcOEt. The organic phase was dried on anhydrous $Na_2SO_4$ and filtered and the solvent evaporated in vacuo. 0.450 g of product were obtained (yield: 95%); Mp: 103-104° C.; TLC: silica gel, eluent $CHCl_3/CH_3OH$ 9.8/0.2, Fr: 0.13; $^1$H NMR ($CDCl_3$, 300 MHz) δ: 7.80 (m, 3H), 7.70 (s, 1H), 7.40 (m, 5H), 6.80 (d, 2H), 4.20 (t, 2H), 3.20 (t, 2H), 1.50 (s, 6H); HPLC: Column: Inertisil ODS 3 (5 µm) 4.6×250 mm, T: room temperature, mobile phase $CH_3CN/KH_2PO_4$ 50 mM 75/25 (v/v), pH: as is, flow rate: 0.75 mL/min, 205 nm UV detector, retention time 13.10 min; E.A. conforming for $C_{22}H_{22}O_3S$.

EXAMPLE 20

Preparation of methyl 2-[4-[2-(1-(5-methoxy)indolil)ethoxy]phenylthio]isobutyrate (ST2577)

Method B

To a solution of ST1923 (prepared as described in example 3) (0.2 g, 0.88 mmoles) in anhydrous THF (6 mL), were added 2-(5-methoxy-indol-1-yl)-ethanol (prepared as described in example 8 starting from 5-methoxy indole and 2-bromo-ethanol) (0.185 g, 0.97 mmoles), DIAD (0.230 g, 1.14 mmoles) and, triphenyl phosphine (0.299 g, 1.14 mmoles) in small portion. The reaction mixture was left overnight under magnetic stirring at room temperature, then the solvent was removed under vacuum and the residue was dissolved in AcOEt and washed with NaOH 1N. The organic phase was dried on $Na_2SO_4$ filtered and evaporated. The residue obtained was purified by silica gel chromatography using as eluent exane/AcOEt 87/13 to give 0.180 g of final product (yield 51%). TLC: silica gel, eluent: exane/AcOEt 7/3, Fr: 0.39; $^1H$ NMR (300 MHz, $CDCl_3$) δ 7.30 (m, 3H), 7.15 (d, 1H), 7.10 (d, 1H), 6.90 (dd, 1H), 6.78 (d, 2H), 6.40 (d, 1H), 4.50 (t, 2H), 4.25 (t, 2H), 3.85 (s, 3H), 3.65 (s, 3H), 1.40 (s, 6H); HPLC: Column: Inertisil ODS 3 (5 μm) 4.6×250 mm, R.T., mobile phase $CH_3CN/H_2O$ 85/15 v/v, pH as it is, flow rate 0.75 mL/min, 205 nm UV detector, retention time 7.80 min; A.E.: conforms to expected for $C_{22}H_{25}NO_4S$.

EXAMPLE 21

Preparation of methyl 2-[4-[2-(1-(5-benziloxy)indolil)etoxy]phenylthio]isobutyrate (ST2562)

Method B

To a solution of ST1923 (prepared as described in example 3) (0.2 g, 0.88 mmoles) in anhydrous THF (6 mL), were added 2-(5-benzyloxy-indol-1-yl)ethanol (prepared as described in example 8 starting from 5-benzyloxy indole and 2-bromo-ethanol) (0.26 g, 0.97 mmoles), DIAD (0.230 g, 1.14 mmoles) and, triphenyl phosphine (0.299 g, 1.14 mmoles) in small portion. The reaction mixture was left overnight under magnetic stirring at room temperature, then the solvent was removed under vacuum and the residue was dissolved in AcOEt and washed with NaOH 1N. The organic layer was dried on $Na_2SO_4$ filtered and evaporated under vacuum. The residue obtained was purified by silica gel chromatography using as eluent exane/AcOEt 85/15 to give 0.240 g of final product (yield 57%). MP: 87-88° C.; TLC: silica gel, eluent: exane/AcOEt 7/3, Fr 0.41; $^1H$ NMR (300 MHz, $CDCl_3$) δ 7.45-7.2 (m, 10H), 7.00 (dd, 1H), 6.80 (d, 2H), 6.40 (d, 1H), 5.10 (s, 2H), 4.50 (t, 2H), 4.25 (t, 2H), 3.60 (s, 3H), 1.40 (s, 6H); HPLC: Column: Inertisil ODS 3 (5 μm) 4.6×250 mm, R.T., mobile phase $CH_3CN/H_2O$ 90/10 v/v, pH as it is, flow rate 0.80 mL/min, 205 nm UV detector, retention time 8.21 min; A.E.: conforms to expected for $C_{28}H_{29}NO_4S$.

EXAMPLE 22

Preparation of methyl 2-[3-[5-(4-nitrophenyl)furfuryloxy]phenylthio]isobutyrate (ST2501)

Method B

To a solution of methyl 2-(3-hydroxy-phenylthio)isobutyrate (prepared as described in example 1) (1.02 g, 4.5 mmoles) in anhydrous THF (23 mL), were added 5-nitrofurfuryl alcohol (0.986 g, 4.5 mmoles), DIAD (1.18 g, 5.85 mmoles) and, triphenyl phosphine (1.53 g, 5.85 mmoles) in small portion. The reaction mixture was left overnight under magnetic stirring at room temperature, then the solvent was removed under vacuum and the residue was dissolved in AcOEt and washed with NaOH 1N. The organic layer was dried on $Na_2SO_4$ filtered and removed under vacuum. The residue obtained was purified by silica gel chromatography using as eluent exane/AcOEt 9.4/0.6 to give 0.380 g of final product (yield 20%). MP: 81-82° C.; TLC: silica gel, eluent: exane/AcOEt 7/3, Fr 0.45; $^1H$ NMR (300 MHz, $CDCl_3$) δ 8.22 (d, 2H), 7.80 (d, 2H), 7.22 (m, 2H), 7.10-7.00 (m, 3H), 6.80 (d, 1H), 6.60 (d, 1H), 5.10 (s, 2H), 370 (s, 3H), 1.50 (s, 6H); HPLC: Column: Symmetry $C_{18}$ (5 μm) 4.6×250 mm, R.T., mobile phase $CH_3CN/H_2O$ 85/15 v/v, pH as it is, flow rate 0.85 mL/min, 205 nm UV detector, retention time 6.24 min; A.E.: conforms to expected for $C_{22}H_{21}NO_6S$.

EXAMPLE 23

Preparation of 2-[4-[2-(1-(5-methoxy)indolil)ethoxy]phenylthio]isobutiric acid (ST2733)

Method A (Step 2)

To a solution of ST2577 (prepared as described in example 20) (0.2 g, 0.50 mmoles) in $CH_3OH$ (3.2 mL), was added a solution of NaOH 1N (6 mL). The reaction mixture was left overnight under magnetic stirring at 40° C., then the organic phase was removed under vacuum and the aqueous phase was extracted with AcOEt. The aqueous layer was separated and acidified with HCl 1N and then extracted again with AcOEt. This second organic extract was washed with water dried on $Na_2SO_4$ filtered and evaporated under vacuum to give 0.138 g of final product (yield 72%). MP: 100-102° C.; TLC: silica gel, eluent: $CHCl_3/CH_3OH$ 8/2, Fr: 0.62; $^1H$ NMR (300 MHz, $CDCl_3$) δ 7.40 (d, 2H), 7.25 (s, 1H), 7.10 (d, 2H), 6.90 (d, 1H), 6.78 (d, 2H), 6.40 (d, 1H), 4.50 (t, 2H), 4.20 (t, 2H), 3.80 (s, 3H), 1.40 (s, 6H); HPLC: Column: Inertisil ODS 3 (5 μm) 4.6×250 mm, R.T., mobile phase $CH_3CN/KH_2PO_4$ 50 mM 70/30, pH as it is, flow rate 1 mL/min, 205 nm UV detector; retention time 7.32 min; A.E.: conforms to expected for $C_{21}H_{23}NO_4S$.

EXAMPLE 24

Preparation of 2-[4-[2-(1-(5-benzyloxy)indolil)ethoxy]phenylthio]-2-methylpropanoic acid (ST2740)

Method A (Step 2)

To a solution of ST2562 (prepared as described in example 21) (0.430 g, 0.90 mmoles) in $CH_3OH$ (10 mL), was added a solution of NaOH 1N (15 mL). The reaction mixture was left 48 hours under magnetic stirring at 40° C., then the organic phase was removed under vacuum and the aqueous residue was extracted with AcOEt. The aqueous phase was separated and acidified with HCl 1N and then extracted again with AcOEt. This second organic extract was washed with water, dried on $Na_2SO_4$ and evaporated under vacuum to give 0.310 g of final product (yield 74%). MP: 160-162° C.; TLC: silica gel, eluent: $CHCl_3/CH_3OH$ 9/1, Fr.: 0.57; $^1H$ NMR (300 MHz, $CDCl_3$) δ 7.40-7.15 (m, 10H), 7.20 (s, 2H), 7.00 (d, 1H), 6.90 (d, 2H), 6.40 (s, 1H), 5.15 (s, 2H), 4.50 (t, 2H), 4.20 (t, 2H), 1.40 (s, 6H); HPLC: Column: Inertisil ODS 3 (5 μm) 4.6×250 mm, R.T., mobile phase: $CH_3CN/KH_2PO_4$ 50 mM 70/30, pH as it is, flow rate 1 mL/min, 205 nm UV detector, retention time 11.60 min; A.E. conforms to expected for $C_{27}H_{27}NO_4S$.

EXAMPLE 25

Preparation of 2-methyl-2-[3-[5-(4-nitrophenyl)furfuryloxy]phenylthio]propanoic acid (ST2753)

Method A (Step 2)

To a solution of ST2501 (prepared as described in example 22) (0.4 g, 0.93 mmoles) in $CH_3OH$ (10 mL), was added a solution of NaOH 1N (25 mL). The reaction mixture was left 4 days under magnetic stirring at 40° C., then the organic phase was removed under vacuum and the aqueous residue was extracted with AcOEt. The aqueous phase was separated and acidified with HCl 1N and then extracted again with AcOEt. This second organic extract was washed with water, dried on $Na_2SO_4$ and evaporated under vacuum. The residue was purified by silica gel chromatography eluting with $CHCl_3/CH_3OH$ 9.4/0.6 to give 0.215 g of final product (yield 56%). MP: 137-138° C.; TLC: silica gel, eluent: $CHCl_3/CH_3OH$ 9/1, Fr 0.53; $^1H$ NMR (300 MHz, DMSO) δ 8.30 (d, 2H), 8.00 (d, 2H), 7.40 (m, 2H), 7.10 (d, 3H), 6.80 (s, 1H), 4.20 (s, 2H), 1.40 (s, 6H); HPLC: Column: Inertisil ODS 3 (5 μm) 4.6×250 mm, R.T., mobile phase $CH_3CN/KH_2PO_4$ 50 mM 70/30, pH as it is, flow rate 1 mL/min, 205 nm UV detector, retention time 11.38 min; A.E.: conforms to expected for $C_{21}H_{19}NO_6S$.

EXAMPLE 26

Antidiabetic and Serum-Lipid-Lowering Activity in the db/db Mouse

Mutations in laboratory animals have made it possible to develop models presenting non-insulin-dependent diabetes associated with obesity, hyperlipidaemia and insulin resistance and that enable us to test the efficacy of new antidiabetes compounds (Reed and Scribner, *Diabetes, obesity and metabolism* 1: 75-86, 1999).

A genetically diabetic mouse model widely used is the C57BL/KsJ db/db mouse.

The genetic basis of this model is a defect in the leptin receptor gene (db/db mouse), which causes leptin resistance and leads to overeating, obesity, hyperinsulinaemia and insulin resistance, with subsequent symptoms of insufficient insular secretion and hyperglycaemia (Kodama et al., *Diabetologia* 37: 739-744, 1994; Zhang et al., *Nature* 372: 425-432, 1994; Chen et al., *Cell* 84: 491-495, 1996).

Since hyperglycaemia is accompanied by obesity and insulin resistance, the db/db mouse presents characteristics that resemble those of type 2 diabetes in human subjects and is useful for assaying insulin-sensitising compounds.

The C57BL/KsJ db/db mice used in the experiments were supplied by Jackson Lab (via Ch. River). After 10 days' acclimatisation in standard conditions (22±2° C.; 55±15% humidity; 15-20 air changes/hour; 12-hour light-darkness cycle with light from 7 a.m. to 7 p.m.) on a standard 4 FR21 diet (Mucedola), blood samples were taken in postabsorption conditions (fasting from 8.30 a.m. to 4.30 p.m.) from the caudal vein with the aid of a Jelco 22G catheter (Johnson and Johnson). Plasma levels of glucose, insulin, triglycerides, cholesterol, free fatty acids and urea were checked for a well-matched distribution of mice in the treatment groups.

At the start of treatment the body weights of the mice were checked and arrangements were made for monitoring water and feed consumption.

The mice were treated orally twice daily (at 8.30 a.m. and 6.30 p.m.) for 25 days (Experiment I) or for 12 days (Experiment II) with the compounds according to the invention, using as reference compounds rosiglitazone, bezafibrate and fenofibrate (Experiment I) or the compound as in example 1 (Experiment II).

The compounds were administered at a dose equivalent to 25 mg/kg of the compound ST2195 of example 1 according to the invention, in 10 ml/kg of vehicle (CMC 1% containing Tween 80 0.5% in deionized $H_2O$). In particular, rosiglitazone was administered at the dose of 5 mg/kg (Lohray et al. *J. Med Chem* 41, 1619-1630, 1998), bezafibrate at 24.8 mg/kg and fenofibrate at 24.7 mg/kg.

In the course of the experiment, serum glucose levels, oral glucose tolerance test (OGTT) findings, a number of lipid status parameters and weight gain were monitored.

The compounds according to the invention proved capable of lowering serum glucose levels in feeding (Table 1), postabsorption (Tables 2, 2a, 5 and 5a) and fasting conditions (Tables 3 and 3a).

They also proved capable of improving glucose tolerance (Tables 4 and 4a) and of reducing fructosamine, an index of protein glycosylation (Tabella 5) which, as mentioned above, plays an important role in the development of the micro- and macrovascular complications of diabetes.

The compounds according to the invention also show a good ability to reduce serum triglyceride levels, similar to that of rosiglitazone and fenofibrate (Tables 6 and 6a).

In addition, unlike rosiglitazone, the compounds according to the invention increased HDL-cholesterol levels (Tables 6 and 6a) and brought about a lower weight gain than that caused by rosiglitazone and one close to that induced by fibrates (Table 7 and 7a).

An increase in HDL-cholesterol values constitutes an indicator of PPARα agonism and of a lower risk of atherosclerosis. PPARα agonism, in fact, increases fatty acid oxidation in tissues, reducing the accumulation of intracellular triglycerides, which favour insulin resistance (Virkamäki et al., *Diabetes* 50, 2337-2343, 2001; Mensink et al., Diabetes 50, 2545-2554, 2001; Kelley and Goodpaster, *Diabetes Care* 24, 933-941, 2001).

TABLE 1

(Experiment I)
Glucose levels in the blood of db/db mice treated orally twice daily with the compound as in example 1, with fibrates (at doses equivalent to 25 mg/kg of the compound as in example 1) and with rosiglitazone (5 mg/kg), after 12 days' treatment. Samples taken in the feeding state, approximately 15 hours after the last treatment. Mean values ± S.E. and variation (%) vs control.

| Compound | Dose mg/kg | Glucose mg/dl | Variation % |
| --- | --- | --- | --- |
| Control | | 487 ± 25 | |
| Rosiglitazone | 5.0 | 365 ± 64 | −25 |
| Bezafibrate | 24.8 | 503 ± 21 | +3 |
| Fenofibrate | 24.7 | 466 ± 8 | −4 |
| Example 1 | 25.0 | 303 ± 16▲ | −38 |

Number of animals per group: 6.
Student's t-test: ▲ indicates P < 0.001 vs control.

TABLE 2

(Experiment I)
Glucose levels in the blood of db/db mice treated orally twice daily with the compound as in example 1, with fibrates (at doses equivalent to 25 mg/kg of the compound as in example 1) and with rosiglitazone (5 mg/kg), after 12 days' treatment. Samples taken in the postabsorption condition (fasting from 9 a.m. to 5 p.m.) and 8 hours after the last treatment.
Mean values ± S.E. and variation (%) vs control.

| Compound | Dose mg/kg | Glucose mg/dl | Variation % |
|---|---|---|---|
| Control | | 414 ± 11 | |
| Rosiglitazone | 5.0 | 314 ± 33□ | −24 |
| Bezafibrate | 24.8 | 421 ± 30 | +2 |
| Fenofibrate | 24.7 | 409 ± 11 | −1 |
| Example 1 | 25.0 | 216 ± 16▲ | −48 |

Number of animals per group: 6.

Student's t-test: □ and ▲ indicate $P < 0.05$ and $P < 0.001$, respectively, vs control.

TABLE 2a (Experiment II)
Glucose levels in the blood of db/db mice treated orally twice daily with the compound as in example 1 and as in example 2 (at a dose equivalent to 25 mg/kg of the compound as in example 1) after 9 days' treatment. Samples taken in the postabsorption condition (fasting from 9 a.m. to 5 p.m.) and 8 hours after the last treatment.
Mean values ± S.E. and variation (%) vs control.

| Compound | Dose mg/kg | Glucose mg/dl | Variation % |
|---|---|---|---|
| Control | | 351 ± 23 | |
| Example 1 | 25.0 | 223 ± 20Δ | −36 |
| Example 2 | 24.0 | 155 ± 21▲ | −66 |

Number of animals per group: 6.
Student's t-test: Δ and ▲ indicate $P < 0.01$ and $P < 0.001$, respectively, vs control.

TABLE 3

(Experiment I)
Glucose levels in the blood of db/db mice treated orally twice daily with the compound as in example 1, with fibrates (at doses equivalent to 25 mg/kg of the compound as in example 1) and with rosiglitazone (5 mg/kg), after 18 days' treatment. Samples taken in the fasting state for 18 hours and at 6 hours after the last treatment.
Mean values ± S.E. and variation (%) vs control.

| Compound | Dose mg/kg | Glucose mg/dl | Variation % |
|---|---|---|---|
| Control | | 344 ± 35 | |
| Rosiglitazone | 5.0 | 225 ± 27■ | −35 |
| Bezafibrate | 24.8 | 298 ± 21 | −13 |
| Fenofibrate | 24.7 | 384 ± 20 | +12 |
| Example 1 | 25.0 | 144 ± 3Δ | −58 |

Number of animals per group: 6.
Student's t-test: ■ and Δ indicate $P < 0.02$ and $P < 0.01$, respectively, vs control.

TABLE 3a (Experiment II)
Glucose levels in the blood of db/db mice treated orally twice daily with the compound as in example 1 and as in example 2 (at a dose equivalent to 25 mg/kg of the compound as in example 1) after 11 days' treatment. Samples taken in the fasting condition for 18 hours and at 5 hours after the last treatment.
Mean values ± S.E. and variation (%) vs control.

| Compound | Dose mg/kg | Glucose mg/dl | Variation % |
|---|---|---|---|
| Control | | 248 ± 18 | |
| Example 1 | 25.0 | 158 ± 7▲ | −36 |
| Example 2 | 24.0 | 128 ± 8▲ | −48 |

Number of animals per group: 6.
Student's t-test: ▲ indicates $P < 0.001$ vs control.

TABLE 4

(Experiment I)
Area under the curve (AUC) for glucose at OGTT in the blood of db/db mice treated orally twice daily with the compound as in example 1, with fibrates (at doses equivalent to the 25 mg/kg of the compound as in example 1) and with rosiglitazone (5 mg/kg), after 18 days' treatment. OGTT (glucose 3 g/kg) in mice fasting for 18 hours and at 5 hours after the last treatment.
Mean values ± S.E. and variation (%) vs control.

| Compound | Dose mg/kg | AUC glucose a.u. | Variation % |
|---|---|---|---|
| Control | | 51182 ± 2392 | |
| Rosiglitazone | 5.0 | 38174 ± 3555Δ | −25 |
| Bezafibrate | 24.8 | 44476 ± 1827 | −13 |
| Fenofibrate | 24.7 | 45192 ± 1546 | −12 |
| Example 1 | 25.0 | 24527 ± 889▲ | −52 |

Number of animals per group: 6.
Student's t-test: Δ and ▲ indicate $P < 0.01$ and $P < 0.001$, respectively, vs control.

TABLE 4a (Experiment II)
Area under the curve (AUC) for glucose at OGTT in the blood of db/db mice treated orally twice daily with the compound as in example 1 and in example 2 (at a dose equivalent to the 25 mg/kg of the compound as in example 1), after 11 days' treatment. OGTT (glucose 3 g/kg) in mice fasting for 18 hours and at 5 hours after the last treatment.
Mean values ± S.E. and variation (%) vs control.

| Compound | Dose mg/kg | AUC glucose a.u. | Variation % |
|---|---|---|---|
| Control | | 43208 ± 2117 | |
| Example 1 | 25.0 | 25929 ± 1299▲ | −40 |
| Example 2 | 24.0 | 24517 ± 2261▲ | −43 |

Number of animals per group: 6.
Student's t-test: ▲ indicates $P < 0.001$ vs control.

TABLE 5

(Experiment I)
Plasma glucose and fructosamine levels in db/db mice treated
orally twice daily with the compound as in example I, with fibrates
(at doses equivalent to 25 mg/kg of the compound as in example 1)
and with rosiglitazone (5 mg/kg), after 25 days' treatment.
Samples taken in postabsorption conditions (fasting from 9 a.m.
to 4.30 p.m.) and 7.5 hours after the last treatment.
Mean values ± S.E. and variation (%) vs control.

| Compound | Dose mg/kg | Glucose mg/dl | Variation % | Fructosamine mM | Variation % |
|---|---|---|---|---|---|
| Control | | 456 ± 45 | | 0.80 ± 0-03 | |
| Rosiglitazone | 5.0 | 296 ± 39■ | −35 | 0.52 ± 0.12 | −35 |
| Bezafibrate | 24.8 | 536 ± 22 | +18 | 1.01 ± 0.04Δ | +26 |
| Fenofibrate | 24.7 | 553 ± 30 | +21 | 0.92 ± 0.02Δ | +15 |
| Example 1 | 25.0 | 206 ± 8Δ | −55 | 0.41 ± 0.04▲ | −49 |

Number of animals per group: 6.
Student's t-test: ■, Δ and σ indicate P < 0.02, P < 0.01 and P < 0.001,
respectively, vs control.

TABLE 5a (Experiment II)
Plasma glucose levels in db/db mice treated orally twice daily
with the compound as in example I and as in example 2 (at a dose
equivalent to 25 mg/kg of the compound as in example 1), after 12 days'
treatment. Samples taken in postabsorption conditions (fasting from 9 a.m.
to 4.30 p.m.) and 7.5 hours after the last treatment.
Mean values ± S.E. and variation (%) vs control.

| Compound | Dose mg/kg | Glucose mg/dl | Variation % |
|---|---|---|---|
| Control | | 576 ± 27 | |
| Example 1 | 25.0 | 356 ± 30▲ | −38 |
| Example 2 | 24.0 | 263 ± 30▲ | −54 |

Number of animals per group: 6.
Student's t-test: ▲ indicates P < 0.001 vs control.

TABLE 6

(Experiment I)
Plasma triglyceride and HDL-cholesterol levels in db/db mice
treated orally twice daily with the compound as in example I, with
fibrates (at doses equivalent to 25 mg/kg of the compound as in
example 1) and with rosiglitazone (5 mg/kg), after 25 days'
treatment.
Samples taken in postabsorption conditions (fasting from 9 a.m.
to 4.30 p.m.) and 7.5 hours after the last treatment.
Mean values ± S.E. and variation (%) vs control.

| Compound | Dose mg/kg | Triglycerides mg/dl | Variation % | HDL-choles. mg/dl | Variation % |
|---|---|---|---|---|---|
| Control | | 95.4 ± 7.2 | | 82.0 ± 6.1 | |
| Rosiglitazone | 5.0 | 43.7 ± 4.1▲ | −54 | 65.4 ± 3.6□ | −20 |
| Bezafibrate | 24.8 | 88.3 ± 12.7 | −7 | 93.8 ± 3.8 | +14 |
| Fenofibrate | 24.7 | 66.5 ± 3.5Δ | −30 | 96.4 ± 4.2 | +18 |
| Example 1 | 25.0 | 45.3 ± 2.3▲ | −53 | 98.0 ± 3.5□ | +20 |

Number of animals per group: 6.
Student's t-test: □, Δ and σ indicate P < 0.05, P < 0.01 and P < 0.001,
respectively, vs control.

TABLE 6a (Experiment II)
Plasma triglyceride and HDL cholesterol levels in db/db mice
treated orally twice daily with the compound as in example I and as
in example 2 (at a dose equivalent to 25 mg/kg of the compound as
in example 1), after 12 days' treatment.
Samples taken in postabsorption conditions (fasting from 9 a.m.
to 4.30 p.m.) and 7.5 hours after the last treatment.
Mean values ± S.E. and variation (%) vs control.

| Compound | Dose mg/kg | Triglycerides mg/dl | Variation % | HDL-choles. mg/dl | Variation % |
|---|---|---|---|---|---|
| Control | | 87.0 ± 3.1 | | 86.4 ± 2.3 | |
| Example 1 | 25.0 | 45.1 ± 1.4▲ | −48 | 123.7 ± 1.9▲ | +43 |
| Example 2 | 24.0 | 48.6 ± 2.5▲ | −44 | 102.5 ± 4.7Δ | +19 |

Number of animals per group: 6.
Student's t-test: Δ and ▲ indicate P < 0.01 and P < 0.001, respectively, vs
control.

TABLE 7

(Experiment I)
Initial and final body weight of db/db mice treated orally twice
daily with the compound as in example 1 and with fibrates (at doses
equivalent to 25 mg/kg of the compound as in example 1) and with
rosiglitazone (5 mg/kg), after 25 days' treatment.
Measurement in postabsorption condition (fasting from 9 a.m.
to 4.30 p.m.).
Mean values ± S.E. and variation (%) vs control.

| Compound | Dose mg/kg | Initial b.w. g | Variation % | Final b.w. g | Variation % |
|---|---|---|---|---|---|
| Control | | 31.7 ± 0.9 | | 28.3 ± 0.8 | |
| Rosiglitazone | 5.0 | 32.6 ± 1.4 | +3 | 42.1 ± 2.5Δ | +49 |
| Bezafibrate | 24.8 | 33.7 ± 0.7 | +6 | 35.2 ± 1.3▲ | +24 |
| Fenofibrate | 24.7 | 33.3 ± 0.7 | +5 | 34.5 ± 1.0▲ | +22 |
| Example 1 | 25.0 | 32.3 ± 0.3 | +2 | 35.9 ± 0.6▲ | +27 |

Number of animals per group: 6.
Student's t-test: Δ and σ indicate P < 0.01 and P < 0.001, respectively, vs
control.

TABLE 7a (Experiment II)
Initial and final body weight of db/db mice treated orally twice
daily with the compound as in example 1 and as in example 2 (at a
dose equivalent to 25 mg/kg of the compound as in example 1),
after 12 days' treatment.
Measurement in postabsorption condition (fasting from 9 a.m.
to 4.30 p.m.).
Mean values ± S.E. and variation (%) vs control.

| Compound | Dose mg/kg | Initial b.w. g | Variation % | Final b.w. g | Variation % |
|---|---|---|---|---|---|
| Control | | 38.8 ± 0.7 | | 37.5 ± 0.6 | |
| Example 1 | 25.0 | 38.6 ± 0.4 | −1 | 40.3 ± 0.8□ | +7 |
| Example 2 | 24.0 | 37.8 ± 0.5 | −3 | 39.4 ± 0.9 | +5 |

Number of animals per group: 6.
Student's t-test: □ indicates P < 0.05 vs control.

EXAMPLE 27

Transient Transfection of Eukaryotic Cells to
Evaluate the Agonist Activity of PPARα Ligands In this example it is demonstrated that the compounds according to the invention are also endowed with PPARα agonist activity.

The identification of PPARα agonists is done by in-vitro screening based on cell biology techniques.

Transactivation assays in eukaryotic cells make it possible to quantitatively evaluate the ability of a hypothetical ligand to favour the interaction of a transcriptional factor with its own response element within a promoter [Sladek R. et al., in: *Nuclear Receptors: A Practical Approach*, Oxford Press pp. 63-68 (1999)].

Since the Peroxisome Proliferator Activated Receptor α (PPARα) exerts its transcriptional modulatory function, its dimerisation with the receptor for 9-cis retinoic acid (RXR) is necessary. The dimer formed is capable of binding to the peroxisome proliferator response element (PPRE), located in the target gene promoter, only if activated by the presence of a ligand of at least one of the two receptors [Berger J. and Moller D. E., *Annu. Rev. Med.* 53, 409-35 (2002)].

A transactivation assay thus requires the simultaneous presence of the following in the preselected cell line:
a) a sufficient amount of PPARα;
b) a sufficient amount of the 9 cis-retinoic acid receptor (RXR);
c) a chimeric plasmid containing the reporter gene controlled by a PPRE, located upstream of a viral heterologous promoter. In our case the reporter gene is chloramphenicol-acetyl transferase (CAT).

Whenever the endogenous levels of PPARα and RXR are insufficient, they can be supplemented from the outside through transfection of expression vectors containing the genes of the receptors concerned [Kersten S. and Wahli W. in: *Nuclear Receptors: A Practical Approach*, Oxford Press pag 74-76 (1999)].

The plasmid pCH110 contains the gene for β-galactosidase and is co-transfected together with the reporter gene CAT, providing the internal control for the efficiency of transfection and the normalisation of the results.

Using this transfection and reporter gene system, however, it is not possible to completely eliminate interference by endogenous receptors constitutively expressed by the cell line used.

An alternative method is therefore used which enables us to get around the problem of interference by possible endogenous receptors.

In this model a transactivation assay is used in which the expression vector mPPARαLBD/Gal4 DBD allows the synthesis by the transfected cell of a chimeric protein, in which the ligand binding domain (LBD) of PPARα is fused with the DNA binding domain (DBD) of the transcription factor GAL4 of yeast [Luckow B. et al., *Nucleic Acids Res.* 15, 5490 (1987)]. Simultaneously, a plasmid (pG5CAT) is transfected which contains 5 copies of the high-affinity binding site for GAL4 (also called UAS, upstream activating sequence), upstream of the viral promoter E1b fused with the CAT reporter gene [Moya-Camarena S. Y. et al., *J. Lipid Res.* 40 (8), 1426-33 (1999)]. This model eliminates interference by possible endogenous receptors.

This is due to the fact that the activation of E1b and the production of CAT will occur exclusively thanks to the interaction of GAL4 DBD with its own response element (UAS). Since the transcription factor GAL4 is not expressed in eukaryotic cells, transactivation of the reporter gene can take place only when, as a result of the interaction of a ligand with the LBD of PPARα, the chimeric protein PPARα/GAL4 recognises the UAS sequence on the plasmid pG5CAT. Together with the expression vector and the reporter vector the cells were also transfected with the plasmid pCH110 which provides the internal control for the efficiency of transfection and the normalisation of the results.

Experimental Procedure

A monkey kidney fibroblast cell line (COS-7) was used [Elbrecht A. et al., *J. Biol. Chem.* 274 (12), 7913-22 (1999)]. The cells were co-transfected with the reporter vector, the expression plasmid coding for the fusion protein Gal4 DBD/PPARαLBD and the control vector pCH110. The cells were exposed to increasing concentrations of the study compounds and CAT activity was evaluated. Untreated cells were used as controls.

Cell Culture

Monkey kidney fibroblasts (COS-7) were cultured according to the usual cell culture techniques, at 37° C. in a 5% v/v carbon dioxide atmosphere using as the growth medium DMEM (Dulbecco's modified Eagle's medium) modified with 3.7 g/l of sodium bicarbonate, 4 mM L-glutamine, 4.5 g/l of glucose, 1 mM sodium pyruvate and 10% v/v of foetal bovine serum, in the presence of streptomycin 100 μg/ml and penicillin 100 U/ml final.

Transient Transfection of COS-7 Cells

The cells were co-transfected using the transfection reagent FuGENE6 (Roche), consisting of a defined mixture of lipids capable of complexing the DNA and of transporting it into the cells. Twenty-four hours prior to transfection the cells were plated at a density of $1.2 \times 10^5$ cells/well in 12-well plates and maintained at 37° C. in a 5% v/v $CO_2$ atmosphere. The culture medium, devoid of serum, was replaced 2 hours before transfection, and then the cells were treated with the transfection reagent FuGENE6 according to the instructions suggested by the supplier. Briefly, the transfection mixture containing 0.8 μg of the expression vector, 1.6 μg of the reporter vector, 0.8 μg of the control vector and 9 μl of the FuGENE6 reagent per well was added directly to the cells in the presence of culture medium devoid of serum. After 5 hours, the transfection medium was replaced by 1 ml of culture medium complete with serum and antibiotics in the presence or absence of the molecules to be tested at 3 different concentrations (2, 20 and 100 μM). Wy-14,643 (2 μM), a known ligand of PPARα, was used as the positive reference compound.

Preparation of Cell Protein Extracts and Assay of Cat Activity

After 48 hours' incubation at 37° C. in a 5% v/v $CO_2$ atmosphere, the cells were washed twice with 1 ml of phosphate buffer (PBS) and removed mechanically from the wells in TEN buffer (Tris[hydroxymethyl]aminomethane 10 mM pH 8, ethylenediamine-tetraacetic acid 1 mM pH 8, sodium chloride 0.1 M). After centrifuging for 3 minutes at 1000 rpm, the cells were resuspended in 65 μl of lysis buffer (Tris-HCl 0.25 M, pH 8) and then lysed thanks to three rapid freeze-thaw cycles. The insoluble cellular materials (debris) were removed by centrifuging at 15,000 rpm for 15 minutes at 4° C., and the supernatant was recovered and used for the CAT and β-galactosidase activity assays.

The cell extracts were stored at −80° C. until assayed after previously adding glycerol (final concentration 10% v/v) and β-mercaptoethanol (final 5 mM) in a final volume of 75 μl.

The assay for evaluating CAT activity was done by applying a variant of the method described by Sleigh [Sleigh M. J. *Annal Biochem.*, 156 (1), 251-6 (1986)]. Briefly, 20 μl of protein cell extract (preheated to 65° C. for 10 minutes to deactivate the internal deacetylating enzymatic activity) were added to a solution containing 10 μl of n-butyryl-Coenzyme A (3.5 mg/ml), 5 μl of [$^{14}$C]-chloramphenicol (0.25 μCi) and 65 μl of distilled $H_2O$. After 2 hours' incubation at 37° C. the reaction was blocked with 200 µl of a solution of xylene/2,6,10,14 tetramethyl-pentadecane (1:2 v/v).

After vigorous stirring and centrifuging for 5 minutes at maximum speed, 150 µl of supernatant were added to 5 ml of scintillation fluid and analysed under the beta-counter (scintillator) to determine the [$^{14}$C] butyryl-chloramphenicol content formed as a result of the enzymatic reaction.

Test for Determining β-Galactosidase Activity

As an internal control for the normalisation of CAT activity in relation to the efficiency of transfection, the β-galactosidase activity coded for by the corresponding gene in the co-transfected plasmid pCH110 was used.

β-galactosidase activity was measured according to a variant of the method described by Sambrook [Sambrook et al. in: *Molecular Cloning, A Laboratory Manual*, Edited by Cold Spring Harbor Laboratory Press (1989)]. Briefly, 20 µl of protein extracts were added to 750 µl of the reaction buffer containing 1 volume of 2 mg/ml ONPG (O-nitrophenyl-β-D-galactopyranoside) and 3 volumes of "Z buffer" (10 mM potassium chloride, 1 mM magnesium chloride, 50 mM β-mercaptoethanol in phosphate buffer). The reaction was run at 37° C. and interrupted by adding 200 µL of a sodium carbonate 1 M solution when the appearance of the typical yellow colouring was clearly noticeable. The samples were incubated for 10 minutes at room temperature and then analysed under the spectrophotometer measuring the absorbance at the wavelength of 420 nm ($A_{420}$).

The following formula was used for the normalisation of the CAT assay results with respect to β-galactosidase activity:

$$\frac{CAT \text{ sample count per minute } (cpm) - \text{blank count per minute } (cpm)}{\beta - galactosidase \text{ units}^*}$$

$$\beta - galactosidase \text{ units}^* = \frac{A_{420} \times \text{dilution factor}}{\text{incubation time (min)}}.$$

Table 8 presents the PPARα agonist activity of the compounds as in examples 1, 2, 4, 10, 13 and 18 by way of examples.

TABLE 8

Assay of transactivation mediated by mPPARαLBD/Gal4DBD in COS-7 cells. The results are expressed as activation of reporter gene CAT as a percentage of that measured in the presence of the reference compound (WY-14,643 2 µM), conventionally assumed to be 100%.

| Compound | Concentration | | |
|---|---|---|---|
| | 2 µM | 20 µM | 100 µM |
| Example 1 | 44.9% | 129.9% | 232.1% |
| Example 2 | 69.7% | 103.6% | 280.9% |
| Example 4 | 113.1% | 284.9% | 421% |
| Example 13 | 132.3% | 199.3% | 203.8% |
| Example 10 | 98.1% | 360% | 462.7% |
| Example 18 | 85% | 96.4% | 151.9% |

EXAMPLE 28

Transient Transfection of Eukaryotic Cells to Evaluate the Agonist Activity of PPARγ Ligands In this example it is demonstrated that a number of compounds according to the invention are also endowed with PPARγ agonist activity.

The identification of PPARγ agonists is done by a specific transactivation assay in eukaryotic cells.

Since the Peroxisome Proliferator Activated Receptor γ (PPARγ) exerts its transcriptional modulatory function, its dimerisation with the receptor for 9-cis retinoic acid is necessary (RXR). The dimer formed is capable of binding to the peroxisome proliferator response element (PPRE), located in the target gene promoter, only if activated by the presence of a ligand of at least one of the two receptors [Berger J. and Moller D. E., *Annu. Rev. Med.* 53, 409-35 (2002)].

A transactivation assay specific for PPARγ thus requires the simultaneous presence of the following in the preselected cell line:
a) a sufficient amount of PPARγ;
b) a sufficient amount of the 9 cis-retinoic acid receptor (RXR);
c) a chimeric plasmid containing the reporter gene controlled by a PPRE, located upstream of a viral heterologous promoter. In our case the reporter gene is chloramphenicol-acetyl transferase (CAT).

In the transactivation assay used, the preselected cells are transfected with the expression vector pSG5 Stop-mPPARg1 which allows the synthesis of the PPARγ receptor by the transfected cell. Simultaneously, a plasmid reporter (pBL-CAT2-PPRE) is transfected which contains a peroxisome proliferator response element (PPRE) isolated by the gene promoter for acyl-CoA oxidase, upstream of the heterologous promoter of viral thymidine kinase (TK) fused with the reporter gene CAT. Since the endogenous cell levels of the RXR receptor are sufficiently high, it is not necessary to transfect an expression vector specific for RXR as well. The expression of the gene coding for CAT is under the control of the TK promoter which does not contain any PPRE. Therefore, any increase in CAT levels will be the result of increased gene transcription dependent upon the dimerisation of PPARγ with RXR and upon the heterodimer bond formed with the peroxisome proliferator response element. Together with the expression vector and the reporter vector the cells are also transfected with the plasmid pCH110 which provides the internal control for the efficiency of transfection and the normalisation of the results Experimental Procedure A cell line of mouse embryonal fibroblasts (NIH-3T3) was used [Hogan J. C. et al., *Biochem Biophys Res Commun.* 287 (2), 484-92 (2001)]. The cells were transfected with the reporter plasmid, the expression plasmid coding for the PPARγ receptor and the control vector pCH110. The cells were exposed to increasing concentrations of the study compounds and CAT activity was evaluated. Untreated cells were used as controls.

Cell Culture

Mouse embryonal fibroblasts (NIH-3T3) were cultured according to the usual cell culture techniques, at 37° C. in a 5% v/v carbon dioxide atmosphere using as the growth medium DMEM (Dulbecco's modified Eagle's medium) modified with 3.7 g/l of sodium bicarbonate, 4 mM L-glutamine, 4.5 g/l of glucose, 1 mM sodium pyruvate and 10% v/v of calf serum, in the presence of streptomycin 100 µg/ml and penicillin 100 U/ml final.

Transient Transfection of NIH-3T3 Cells

The cells were co-transfected using the transfection reagent FuGENE6 (Roche), already described in the previous example. Twenty-four hours prior to transfection the cells were plated at a density of $8.0 \times 10^4$ cells/well in 12-well plates and maintained at 37° C. in a 5% v/v $CO_2$ atmosphere. The culture medium, devoid of serum, was replaced 2 hours before transfection, and then the cells were treated with the transfection reagent FuGENE6, as described in the previous example. After 5 hours, the transfection medium was replaced by 1 ml of culture medium complete with serum and antibiotics in the presence or absence of the molecules to be tested at 3 different concentrations (2, 20 and 100 µM). Rosiglitazone, a known ligand of PPARγ, was used as the positive reference compound.

Preparation of Cell Protein Extracts and Assay of CAT Activity

The cell protein extracts were prepared and the CAT activity assay was conducted exactly as described in the previous example.

Test for Determining β-Galactosidase Activity

As an internal control for the normalisation of the CAT activity in relation to the transfection efficiency, β-galactosidase activity coded for by the corresponding gene in the co-transfected plasmid pCH110 was used.

β-galatosidase activity was measured exactly as described in the previous example.

For the normalisation of the CAT assay results in relation to α-galactosidase activity the formula described in the previous example was used.

Table 9 presents the PPARγ agonist activity of a number of compounds by way of examples.

TABLE 9

Assay of transactivation mediated by PPARγ in NIH-3T3 cells. The results are expressed as activation of the gene-reporter CAT as a percentage of that measured in the presence of the reference compound (rosiglitazone 2 µM), conventionally assumed to be 100%.

| Compound | Concentration | | |
|---|---|---|---|
| | 2 µM | 20 µM | 100 µM |
| Example 2 | 28.6% | 61.2% | 114.3% |
| Example 13 | 61.6% | 91.6% | 101% |
| Example 18 | 25% | 67% | 82.2% |

The results obtained, presented in Tables 1-7a, show that the compounds according to the invention are useful agents for the treatment of diabetes and hyperlipidaemia, for increasing HDL-cholesterol levels, and for preventing and treating the complications relating to diabetes and insulin resistance, for the primary and secondary prevention of CHD, and potentially for the therapy of fatty liver.

The objects of the present invention are pharmaceutical compositions containing as their active ingredient at least one formula (I) compound, either alone or in combination with one or more formula (I) compounds, or, said formula (I) compound or compounds in combination with other active ingredients useful in the treatment of the diseases indicated in the present invention, for example, other products with serum-glucose-lowering and serum-lipid-lowering activity; also in separate dosage forms or in forms suitable for combined therapies. The active ingredient according to the present invention will be in a mixture with suitable vehicles and/or excipients commonly used in pharmacy, such as, for instance, those described in "Remington's Pharmaceutical Sciences Handbook", latest edition. The compositions according to the present invention will contain a therapeutically effective amount of the active ingredient. The doses will be decided by the expert in the sector, e.g. the clinician or primary care physician according to the type of disease to be treated and the patient's condition, or concomitantly with the administration of other active ingredients. By way of an example, dosages ranging from 0.01 to 400 mg/day can be indicated, preferably 0.1 to 200 mg/day.

Examples of pharmaceutical compositions are those that allow administration orally or parenterally—intravenous, intramuscular, subcutaneous, transdermal. Suitable pharmaceutical compositions for the purpose are tablets, rigid or soft capsules, powders, solutions, suspensions, syrups, and solid forms for extempore liquid preparations. Compositions for parenteral administration are, for example, all the forms which are injectable intramuscularly, intravenously, subcutaneously, or in the form of solutions, suspensions or emulsions. Liposomal formulations should also be mentioned. Other forms are tablets for the controlled release of the active ingredient, or for oral administration, tablets coated with appropriate layers, microencapsulated powders, complexes with cyclodextrins, and depot forms, for example, subcutaneous ones, such as depot injections or implants.

What is claimed is:

1. A method for the treatment of hyperglycemia comprising administering to a subject in need of same an effective amount of a compound of formula (I):

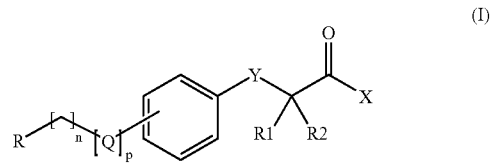

in which

R is —H; aryl or heteroaryl, mono, bicyclic or tricyclic, optionally substituted with one or more halogen groups, nitro, hydroxy, alkyl and alkoxy, optionally substituted with one or more halogen groups;

n is 0-3;

p is 0-1;

X is —OH, —O-alkyl $C_1$-$C_4$;

R1 and R2, which may be the same or different, are selected from: —H; alkyl $C_1$-$C_5$, —COX;

Q is selected from: NH, O, S, —NHC(O)O—, —NHC(O)NH—, —NHC(O)S—, —OC(O)NH—, —NHC(S)O—, —NHC(S)NH—, —C(O)NH—; and Y is S;

and their pharmaceutically acceptable salts, racemic mixtures, single enantiomers, or stereoisomers and tautomers.

2. The method according to claim 1, in which R is an aryl or an aryl substituted with one or more halogen atoms, alkyl, alkoxy or haloalkyl, p is 1, n is 0, 1 or 2, and Q is oxygen.

3. The method according to claim 1, in which R is methyl, methoxy or trifluoromethyl, nitro, mono- or di-alkylamine.

4. The method according to claim 1, in which R is a heteroaryl containing nitrogen as heteroatom bound to the rest of the molecule and p is 1, n is 0, 1 or 2, and Q is oxygen.

5. The method according to claim 1, in which R is 1-indolyl or 1-carbazolyl.

6. The method according to claim 1, in which the compound is selected from the group consisting of:
   i. methyl 2-[3-[2-(4-chlorophenyl)ethoxy]phenylthio]iso-butyrate (ST2195);
   ii. 2-[3-[2-(4-chlorophenyl)ethoxy]phenylthio]-2-methyl-propanoic acid (ST2518);
   iii. methyl 2-[4-[2-(4-chlorophenyl)ethoxy]phenylthio]iso-butyrate (ST1929);
   iv. methyl 2-[3-(2-(2,4-dichlorophenyl)ethoxy)phenylthio]iso-butyrate (ST2534);
   v. methyl 2-[4-(2-(2,4-dichlorophenyl)ethoxy)phenylthio]iso-butyrate (ST2531);
   vi. methyl 2-[3-(2-(carbazol-9-yl)ethoxy)phenylthio]isobutyrate (ST2365);
   vii. methyl 2-[4-(2-(carbazol-9-yl)ethoxy)phenyltho]iso-butyrate (ST2387);
   viii. methyl 2-[4-[2-(1-indolyl)ethoxy]phenylthio]isobutyrate (ST1983);
   ix. methyl 2-[3-[2-(1-indolyl)ethoxy]phenylthio]isobutyrate (ST2394);
   x. methyl 2-[3-[2-(2-naphthyl)ethoxy]phenylthio]iso-butyrate (ST2167);
   xi. methyl 2-[4-[2-(2-naphthyl)ethoxy]phenylthio]isobutyrate (ST2011);
   xii. 2-[4-[2-(4-chlorophenyl)ethoxy]phenylthio]-2-methyl-propanoic acid (ST2505);
   xiii. 2-[3-(2-(2,4-dichlorophenyl)ethoxy)phenylthio]-2-methylpropanoic acid (ST2653);
   xiv. 2-[4-(2-(2,4-dichlorophenyl)ethoxy)phenylthio]-2-methylpropanoic acid (ST2652);
   xv. 2-[3-(2-(carbazol-9-yl)ethoxy)phenylthio]-2-methyl propanoic acid (ST2618);
   xvi. 2-[4-[2-(1-indolyl)ethoxy]phenylthio]-2-methyl propanoic acid (ST2622);
   xvii. 2-[3-[2-(1-indolyl)ethoxy]phenyltho]-2-methyl propanoic acid (ST2651);
   xviii. 2-[3-[2-(2-naphthyl)ethoxy]phenylthio]-2-methyl-propanoic acid (ST2609);
   xix. 2-[4-[2-(2-naphthyl)ethoxy]phenylthio]-2-methyl-propanoic acid (ST2036);
   xx. methyl 2-[4-[2-(1-(5-methoxy)indolil)ethoxy]phenylthio]isobutyrate (ST2577);
   xxi. methyl 2-[4-[2-(1-(5-benziloxy)indolil)etoxy]phenylthio]isobutyrate (ST2562);
   xxii. methyl 2-[3-[5-(4-nitrophenyl)furfuryloxy]phenylthio]isobutyrate (ST2501);
   xxiii. 2-[4-[2-(1-(5-methoxy)indolil)ethoxy]phenylthio]isobutiric acid (ST2733);
   xxiv. 2-[4-[2-(1-(5-benzyloxy)indolil)ethoxy]phenylthio]-2-methylpropanoic acid (ST2740); and
   xxv. 2-methyl-2-[3-[5-(4-nitrophenyl)furfuryloxy]phenylthio]propanoic acid (ST2753).

7. The method according to claim 1, in which the compound is methyl 2-[3-[2-(4-chlorophenyl)ethoxy]phenylthio]isobutyrate (ST2195).

8. The method according to claim 1, in which the method treats diabetes, the microvascular complications of diabetes, or the macrovascular complications of diabetes.

9. The method of claim 8 wherein the diabetes is type 2 diabetes.

10. The method of claim 8 wherein the microvascular complication of diabetes is diabetic retinopathy, diabetic neuropathy or diabetic nephropathy.

11. The method of claim 8 wherein the macrovascular complication is peripheral vasculopathy, myocardial infarction or stroke.

12. The method according to claim 1 in which the method treats syndrome X, polycystic ovary syndrome, obesity, or a form of insulin resistance.

13. The method according to claim 1 in which the method treats fatty liver or NASH (non-alcoholic steatohepatitis).

14. The method of claim 13 in which the fatty liver is NAFLD (non-alcoholic fatty liver disease).

15. The method of claim 1, for the prevention and treatment of hypertension, for the primary and secondary prevention of coronary heart disease (CHD).

16. The method according to claim 1, wherein the hyperglycemia is associated with hyperlipidaemia.

17. The method according to claim 1, in which the compound is administered orally or parenterally.

18. The method according to claim 1, in which the formula (I) compound is administered at a dose ranging from 0.01 to 400 mg.

19. The method according to claim 18 in which the formula (I) compound is administered at a dose ranging from 0.1 to 200 mg.

* * * * *